(12) United States Patent
Senanayake et al.

(10) Patent No.: US 7,064,214 B2
(45) Date of Patent: Jun. 20, 2006

(54) METHODS OF PREPARING SULFINAMIDES AND SULFOXIDES

(75) Inventors: Chris Hugh Senanayake, Shrewsbury, MA (US); Zhengxu Han, Shrewsbury, MA (US); Dhileepkumar Krishnamurthy, Westborough, MA (US); Derek Pflum, Northville, MI (US); Harold Scott Wilkinson, Marlborough, MA (US)

(73) Assignee: Apsinterm LLC, Wilmington, DE (US)

( * ) Notice: Subject to any disclaimer, the term of this patent is extended or adjusted under 35 U.S.C. 154(b) by 844 days.

(21) Appl. No.: 10/120,541

(22) Filed: Apr. 12, 2002

(65) Prior Publication Data

US 2003/0083517 A1 May 1, 2003

Related U.S. Application Data

(60) Provisional application No. 60/283,337, filed on Apr. 13, 2001.

(51) Int. Cl.
*C07D 213/02* (2006.01)
*C07D 235/04* (2006.01)

(52) U.S. Cl. ............ 546/339; 548/122; 548/206; 548/300.1; 548/306.4

(58) Field of Classification Search ............ 562/125; 548/122, 206, 300.1, 306.4; 546/339
See application file for complete search history.

(56) References Cited

U.S. PATENT DOCUMENTS

| 5,714,504 A | * | 2/1998 | Lindberg et al. ............ 514/338 |
| 5,776,765 A | | 7/1998 | Graham et al. |
| 5,945,425 A | * | 8/1999 | Moormann et al. ......... 514/269 |
| 5,948,789 A | | 9/1999 | Larsson et al. |

OTHER PUBLICATIONS

Cogan, Derek A et al, Asymmetric Synthesis of Chiral Amines by Highly Diastereoselective 1,2-Additions of Organometallic Reagents to N-tert-Butanesulfinyl Imines. Tetrahedron 55 (1999) 8883-8904.

Tang, Tony P et al, The tert-Butanesulfinyl Group: An Ideal Chiral Directing Group and Boc-Surrogate for the Asymmetric Synthesis and Applications of beta-Amino Acids. J. Org. Chem. 1999, 64, 12-13.

Liu, Guangcheng et al, Catalytic Asymmetric Synthesis of tert-Butanesulfinamide. Application to the Asymmetric Synthesis of Amines. J. Am. Chem. Soc. 1997, 119, 9913-9914.

Davis, Franklin A et al, Concise Asymmetric Synthesis of alpha-Amino Acid Derivatives from N-Sulfinylimino Esters, J. Org. Chem. 1999, 64, 3396-3397.

Cogan, Derek A, Catalytic Asymmetric Oxidation of tert-Butyl Disulfide. Synthesis of tert-Butanesulfinamides, tert-Butyl Sulfoxides and tert-Butanesulfinimines. Journal of the American Chemical Society. vol. 120, No. 32, Aug. 19, 1998.

Owens, Timothy D et al, Synthesis, Utility and Structure of Novel Bis(sulfinyl)imidoamidine Ligands for Asymmetric Lewis Acid Catalysis. J. Am. Chem. Soc. 2001, 123, 1539-1540.

Kagan, H. B et al, Some Routes to Chiral Sulfoxides with Very High Enantiomeric Excesses. Synlett 643-650, 1990.

Pflum, Derek A et al, Asymmetric Synthesis of Celirizine Dihydrochloride. Tetrahedron Letters 43 (2002) 923-926.

Wudl, F et al, Novel Asymmetric Synthesis of Chiral Sulphoxides. J.C.S. Chem. Comm. 1972, 61-62.

Wudl, F et al, Asymmetric Synthesis of Chiral Sulfoxides. II. An Intramolecular O -> N Sulfinyl Migration. Journal of the American Chemical Society 95:19 Sep. 19, 1973. 6349-6358.

* cited by examiner

*Primary Examiner*—Golam M. M. Shameem
(74) *Attorney, Agent, or Firm*—Martin A Hay

(57) ABSTRACT

This invention encompasses novel methods of preparing sulfinamides and sulfoxides, particularly stereomerically pure sulfinamides and sulfoxides. The invention further encompasses novel compounds from which sulfinamides and sulfoxides can be prepared.

28 Claims, No Drawings

METHODS OF PREPARING SULFINAMIDES AND SULFOXIDES

This application claims priority to U.S. Provisional Application No. 60/283,337, filed Apr. 13, 2001, the entirety of which is incorporated herein by reference.

1. FIELD OF THE INVENTION

This invention relates to sulfinamides and sulfoxides, methods of their preparation, and compounds that can be used to prepare them.

2. BACKGROUND OF THE INVENTION

2.1. The Asymmetric Synthesis of Amines

At least 75% of drugs and drug candidates reportedly incorporate amine functionality. Tang, T. P. and Ellman, J. A., *J. Org. Chem.* 64:12–13 (1999). The asymmetric synthesis of amines is consequently of particular importance to the pharmaceutical industry.

One method that reportedly can be used to prepare optically active β-amino acids is disclosed in International Application WO 2000/041997. According to this method, a compound of the formula RaC*H(OH)—C*H(Rb)Rc, wherein Rc can be $R_1SO_2(R_2)N$— and the asterisk signifies a chiral center, is reportedly prepared by reacting an α-aminocarbonyl compound of the formula Ra—CO—CH(Rb)—Rc with hydrogen or a hydrogen donor in the presence of an optically active transition metal compound and a base.

Another recently reported method of preparing chiral amino acids utilizes sulfinamides. See, e.g., Tang, T. P. and Ellman, J. A., *J. Org. Chem.* 64:12–13 (1999); Cogen, D. A., et al., *Tetrahedron* 55:8883–8904 (1999); Liu, G., et al., *J. Am. Chem. Soc.* 119:9913–9914 (1997); Davis, F. A. and McCoull, W., *J. Org. Chem.* 64:3396–3397 (1999). In an example of this method, tert-butanesulfinamide condenses with aldehydes and ketones to give tert-butanesulfinyl imines in high yields. Tang, T. P. and Ellman, J. A., *J. Org. Chem.* 64:12–13 (1999). These imines can then be contacted with Grignard reagents or organolithiums to provide the intermediate shown below in Scheme I, which can then be subjected to acidic methanolysis to provide an α-branched amine-hydrochloride product. Id.

Scheme I

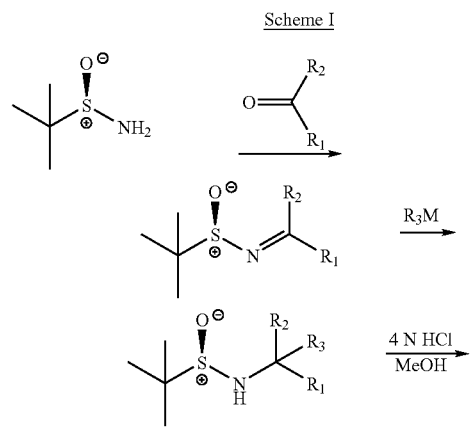

Few methods of preparing enantiomerically pure sulfinamides have been reported. See, e.g., Cogan, D. A., et al., *J. Am. Chem. Soc.* 120:8011–8019 (1998); Liu, G., et al., *J. Am. Chem. Soc.* 119:9913–9914 (1997). In one method, tert-butanesulfinamide is prepared by asymmetrically oxidizing tert-butyl disulfide to provide an intermediate, which is then cleaved by reaction with $LiNH_2$. Liu, G., et al., *J. Am. Chem. Soc.* 119:9913–9914 (1997). Unfortunately, the enantiomeric purity of the resulting sulfinamide reportedly does not exceed 91%. Id. The method is further limited in that it can be used for the synthesis of only a few different kinds of sulfinamides, of which tert-butanesulfinamide is an example. In addition, this method is not amenable to large-scale, or industrial, production of sulfinamides. A need therefore exits for more efficient and effective methods of preparing a wide variety of sulfinamides, particularly enantiomerically pure sulfinamides. A need further exists for a method of preparing sulfinamides that can be adapted to an industrial scale.

2.2. The Asymmetric Synthesis of Sulfoxides

The synthesis of chiral sulfoxides is also important to the pharmaceutical industry. For example, a variety of pharmacologically active benzimidazoles and structurally related sulfoxide compounds contain a stereogenic sulfur atom. Examples of such compounds are shown below in racemic form:

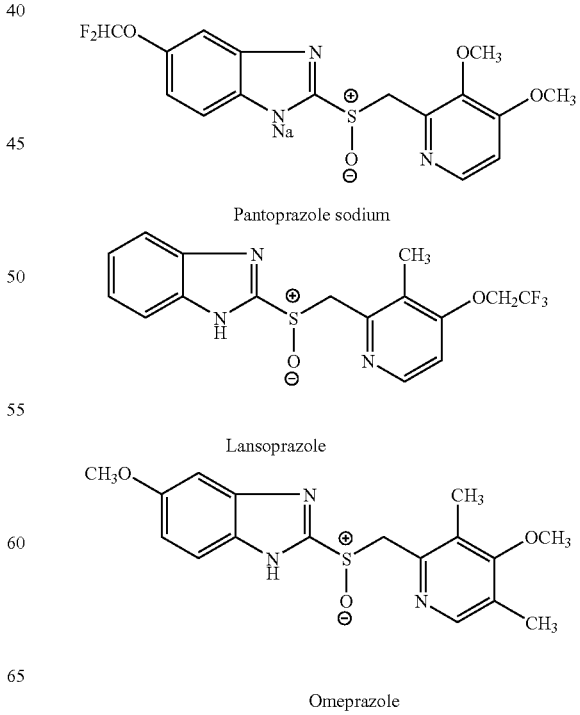

-continued

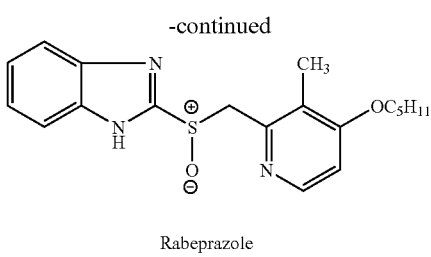

Rabeprazole

Pantoprazole sodium is sold under the tradename Protonix® for the short term treatment of erosive esophagitis associated with gastroesophageal reflux disease (GERD). *Physicians' Desk Reference*, 3439–3442 (55$^{th}$ ed., 2001). Lansoprazole is sold under the tradename Prevacide for the short term treatment of active duodenal ulcer. Id. at 3189–3194. Omeprazole, which is also indicated for the short term treatment of active duodenal ulcer, is sold under the tradename Prilosec®. Id. at 587–591. Finally, rabeprazole is sold under the tradename Aciphex® for the short term treatment of erosive or ulcerative GERD, for maintaining healing and reduction in relapse rates of heartburn symptoms in patients with erosive or ulcerative GERD, for the short-term healing of active duodenal ulcer, and for the long-term treatment of pathological hypersecretroy conditions. Id. at 1178–1181.

Various attempts have been made to obtain enantiomerically pure forms of sulfoxide compounds such as these. Initial attempts relied on chromatography and the formation of chiral salts. See, e.g., U.S. Pat. Nos. 5,693,818 and 5,714,504. Methods for the asymmetric syntheses of sulfoxides have also been alleged. For example, U.S. Pat. No. 5,776,765 discloses a process that can allegedly be used for the enantiomeric synthesis of omeprazole, which comprises the use of a microbial enzyme system to enantioselectively reduce a racemic sulfoxide compound. See, e.g., col. 12, line 57-col. 13, line 67. A method disclosed by U.S. Pat. No. 5,948,789 comprises the oxidation of a pro-chiral sulphide using a chiral titanium complex and a base. See, e.g., col. 25, line 64-col. 27, line 8.

A need exists for new methods of preparing stereomerically pure (e.g., enantiomerically pure) sulfoxides. A particular need exists for efficient and effective methods of preparing enantiomerically pure sulfoxides that can be adapted to an industrial scale.

3. SUMMARY OF THE INVENTION

This invention is directed, in part, to novel methods of preparing sulfinamides and sulfoxides, particularly stereomerically pure sulfinamides and sulfoxides. The invention further encompasses novel compounds from which sulfinamides and sulfoxides can be prepared. Compounds of this invention can be used in the preparation of biologically active (e.g., pharmacologically active) compounds, or are themselves biologically active and useful in the treatment or prevention of diseases or conditions in animals (e.g., humans).

3.1. Definitions

As used herein, the term "prodrug" means a derivative of a compound that can hydrolyze, oxidize, or otherwise react under biological conditions (in vitro or in vivo) to provide the compound. Examples of prodrugs include, but are not limited to, derivatives of 2-(2-pyridylmethyl)sulfinyl)benzimidazoles that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of 2-(2-pyridyhnethyl)sulfinyl)benzimidazoles that comprise —NO, —NO$_2$, —ONO, and —ONO$_2$ moieties.

As used herein, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically less active or inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "biohydrolyzable ester" means an ester of a compound that either: 1) does not interfere with the biological activity of the compound but can confer upon that compound advantageous properties in vivo, such as uptake, duration of action, or onset of action; or 2) is biologically less active or inactive but is converted in vivo to the biologically active compound. Examples of biohydrolyzable esters include, but are not limited to, lower alkyl esters, acyl esters (e.g., —C(O)Z, wherein Z is F, C, Br, I), alkoxyacyloxy esters, alkyl acylamino alkyl esters, and choline esters.

As used herein, the term "biohydrolyzable amide" means an amide of a compound that either: 1) does not interfere with the biological activity of the compound but can confer upon that compound advantageous properties in vivo, such as uptake, duration of action, or onset of action; or 2) is biologically less active or inactive but is converted in vivo to the biologically active compound. Examples of biohydrolyzable amides include, but are not limited to, lower alkyl amides, α-amino acid amides, alkoxyacyl amides, substituted and unsubstituted ureas, and alkylaminoalkylcarbonyl amides.

As used herein, the term "pharmaceutically acceptable salt" refers to a salt prepared from a pharmaceutically acceptable non-toxic inorganic or organic acid. Suitable non-toxic acids include, but are not limited to, acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. For example, specific pharmaceutically acceptable salts are hydrochloride, maleic acid, and tartaric acid salts.

As used herein and unless otherwise indicated, the term "alkyl" includes saturated linear, branched, and cyclic hydrocarbon radicals having 1 to 20 carbon atoms, 1 to 12, 1 to 8, or 1 to 4 carbon atoms. An alkyl group can include one or more double or triple bonds or can be substituted with one or more heteroatoms or halogens (e.g., F, Cl, Br, I). It is understood that cyclic alkyl groups comprise at least three carbon atoms. Specific examples of branched alkyl have one or two branches. Unsaturated alkyl have one or more double bonds and/or one or more triple bonds. Specific examples of unsaturated alkyl have one or two double bonds or one triple bond. Alkyl chains may be unsubstituted or substituted with from 1 to 4 substituents. Specific examples of substituted alkyl are mono-, di-, or trisubstituted alkyl. Specific examples of alkyl substituents include halo, haloalkyl, hydroxy, aryl (e.g., phenyl, tolyl, alkyloxphenyl, alkyloxycarbonylphenyl, halophenyl), beterocyclyl, and heteroaryl.

As used herein and unless otherwise indicated, the term "lower alkyl" means branched or linear alkyl having from 1 to 8 or from 1 to 4 carbon atoms. Examples include, but are not limited to, methyl, ethyl, propyl, isopropyl, isobutyl, and tertiary butyl.

As used herein and unless otherwise indicated, the term "heteroalkyl" means a saturated or unsaturated chain containing carbon and at least one heteroatom, wherein no two heteroatoms are adjacent. Heteroalkyl chains contain from 1 to 18, 1 to 12, 1 to 6, or 1 to 4 member atoms (carbon and heteroatoms) in the chain. Heteroalkyl chains may be straight or branched. Specific examples of branched heteroalkyl have one or two branches. Unsaturated heteroalkyl have one or more double bonds and/or one or more triple bonds. Specific examples of unsaturated heteroalkyl have one or two double bonds or one triple bond. Heteroalkyl chains may be unsubstituted or substituted with from 1 to about 4 substituents. Specific examples of heteroalkyl are substituted or unsubstituted. Specific examples of heteroalkyl substituents include halo, hydroxy, aryl (e.g., phenyl, tolyl, alkyloxphenyl, alkyloxycarbonylphenyl, halophenyl), heterocyclyl, and heteroaryl. For example, alkyl substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di- $C_1$–$C_3$ alkanylamino, methylphenylamino, methylbenzylamino, $C_1$–$C_3$ alkanylamido, carbamamido, ureido, guanidino).

As used herein and unless otherwise indicated, the term "heteroatom" includes a nitrogen, sulfur, oxygen, or phosphorus atom. Groups containing more than one heteroatom may contain different heteroatoms.

As used herein and unless otherwise indicated, the term "aryl" includes an organic radical derived from an aromatic hydrocarbon by removal of one hydrogen, such as phenyl or naphthyl. Aryl rings are monocyclic or fused bicyclic ring systems. Monocyclic aromatic rings contain from about 5 to about 10 carbon atoms, from 5 to 7 carbon atoms, or from 5 to 6 carbon atoms in the ring. Bicyclic aromatic rings contain from 8 to 12 carbon atoms, or 9 or 10 carbon atoms in the ring. Aromatic rings may be unsubstituted or substituted with from 1 to about 4 substituents on the ring. Specific examples of aromatic ring substituents include: halo, cyano, alkyl, heteroalkyl, haloalkyl, phenyl, phenoxy or any combination thereof. More Specific examples of substituents include halo and haloalkyl. Specific examples of aromatic rings include naphthyl and phenyl.

As used herein and unless otherwise indicated, the term "aralkyl" means an aryl substituted with one or more linear, branched, or cyclic alkyl groups. Aralkyl moieties can be attached to other moieties through their aryl or alkyl components.

As used herein and unless otherwise indicated, the term "ether" includes alkyl groups wherein at least one carbon atom has been replaced with an oxygen atom, and aralkyl groups wherein at least one non-aromatic carbon atom has been replaced with an oxygen atom.

As used herein and unless otherwise indicated, the terms "heterocyclic group" and "heterocycle" include aromatic and non-aromatic heterocyclic groups containing one or more heteroatoms each selected from O, S, N, or P. Non-aromatic heterocyclic groups include groups having only 3 atoms in their ring system, but aromatic heterocyclic groups (i.e., heteroaryl groups) must have at least 5 atoms in their ring system. Heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl, and an example of a 10 membered heterocyclic group is quinolinyl. Examples of non-aromatic heterocyclic groups include, but are not limited to, pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, and substituted derivative thereof. Examples of aromatic heterocyclic groups include, but are not limited to, pyridinyl, methylpyridine analgoues, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzoimidazoles, benzofuranyl, cinnolinyl, indazolyl, indolinyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and substituted derivatives thereof. The foregoing groups, as derived from the compounds listed above, may be C-attached or N-attached where such -attachment is possible. For instance, a group derived from benzimidazol can be -benzimidazol-1-yl (N-attached) or benzimidazol-2-yl (C-attached).

As used herein and unless otherwise indicated, the term "heteroaryl" means an aromatic heterocycle. A heteroaryl is an aromatic ring system containing carbon and from 1 to about 4 heteroatoms in the ring. Heteroaromatic rings are monocyclic or fused bicyclic ring systems. Monocyclic heteroaromatic rings contain from about 5 to about 10, from 5 to 7, or from 5 to 6 member atoms (carbon and heteroatoms). Bicyclic heteroaromatic rings contain from 8 to 12 9 or 10 member atoms. Heteroaromatic rings may be unsubstituted or substituted with from 1 to about 4 substituents on the ring. Specific examples of heteroaromatic ring substituents include: halo, cyano, alkyl, heteroalkyl, haloalkyl, phenyl, phenoxy or any combination thereof. More Specific examples of substituents include halo, haloalkyl, and phenyl. Specific examples of heteroaromatic rings include thienyl, thiazolo, purinyl, pyrimidyl, pyridyl, and furanyl.

As used herein and unless otherwise indicated, the term "sulfide" includes alkyl groups wherein at least one carbon atom has been replaced with a sulfur atom, and aralkyl groups wherein at least one non-aromatic carbon atom has been replaced with a sulfur atom.

As used herein and unless otherwise indicated, the term "substituted" as used to describe a compound or chemical moiety means that at least one hydrogen atom of that compound or chemical moiety is replaced with a second chemical moiety. Examples of second chemical moieties include, but are not limited to: halogen atoms (e.g., chlorine, bromine, and iodine); $C_1$–$C_6$ linear, branched, or cyclic alkyl (e.g., methyl, ethyl, butyl, tert-butyl, and cyclobutyl); hydroxyl; thiols; carboxylic acids; esters, amides, silanes, nitriles, thioethers, stannanes, and primary, secondary, and tertiary amines (e.g., —$NH_2$, —$NH(CH_3)$, —$N(CH_3)_2$, and cyclic amines). Specific examples of second chemical moieties are chlorine, hydroxyl, methoxy, amine, thiol, and carboxylic acid.

As used herein and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diasteroemers of the compound. A typical stereomerically pure compound comprises greater than about 80% by weight of stereoisomer of the compound and less than about 20% by weight of other stereoisomers the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein and unless otherwise indicated, the term "polymer bound" and "polymer bound alkyl or aryl" mean that the compound of the invention is covalently bound to a polymer support, such as, but not limited to, Merrifield Resin, See Wang et al., *J. Org. Chem*, 1977, 42, 1286–1290; Wang Resin, See Fancelli et al., *Tetrahedron Lett.*, 1997, 38, 2311–2314; Aminomethyl Resin; MBHA Resin; Amino Acid-2-Chlorotrityl Resin; Carboxypolystyrene; 4-Nitrophenyl Carbonate Resin; Oxime Resin; Safety-Catch Resin; Alkenyl based resins; Br, Cl functionalized resins; Carbonate resins; CHO functionalized resins; $CO_2H$ functionalized resins; Diazonium-based resins; Enol functionalized resins; $NH_2$, $NH_2NH$ functionalized resins; OH functionalized resins; Orthogonal photocleavable resins; SH functionalized resins; Silylalkyl resins; Silyloxy resins; Triazene-based resins; Polymer-bound bases (e.g., (Polystyrylmethyl)trimethylammonium bicarbonate, Morpholinomethyl polystyrene HL, Piperazinomethyl polystyrene, Piperidine-4-carboxylic acid polyamine resin, Piperidinomethyl polystyrene, TBD-methyl polystyrene, Tris-(isonipecotylaminoethyl)-amine polystyrene); Polymer-bound coupling reagents (e.g., Ethoxycarbonylazocarboxymethyl polystyrene, HOBt-6-carboxamidomethyl polystyrene, N-Cyclohexylcarbodiimide, N'-methyl polystyrene); Polymer-bound oxidizing reagents (e.g., Polystyrylmethyl)trimethylammonium meta-periodate, (Polystyrylmethyl)trimethyl-ammonium perruthenate, 4-(Polystyrylmethyloxy)-2,2,6,6-tetramethyl-piperidin-1-yloxy free radical, 6-(Methylsulfinyl)hexanoylmethyl polystyrene, TEMPO polystyrene); Polymer-bound phosphines (e.g., Di(n-butyl)phenylphosphine polystyrene, Di-o-tolylphenylphosphine polystyrene, Dicyclohexylphenylphosphine polystyrene, Diphenylphosphinobenzoyl NovaGel™ AM resin, Diphenylphosphinomethyl polystyrene, Diphenylphosphinopolystyrene, Triphenylphosphine NovaGel™, Triphenylphosphine polystyrene); or Polymer-bound reducing agents (e.g., (Polystyrylmethyl)trimethylammonium borohydride, (Polystyrylmethyl)trimethylammonium cyanoborohydride, Dimethylsilyl polystyrene).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4. DETAILED DESCRIPTION OF THE INVENTION

This invention is directed, in part, to novel methods of preparing sulfinamides and sulfoxides. These methods can be used, for example, to provide sulfinamides such as, but riot limited to, stereomerically pure forms of tert-butanesulfinamide, and sulfoxides such as, but not limited to, stereomerically pure forms of compounds disclosed by U.S. Pat. No. 5,776,765 (e.g., 2-(2-pyridylmethyl)sulfinyl)benzimidazoles) and U.S. Pat. No. 5,945,425 (e.g., ($H^+$/$K^+$) ATPase inhibitors), both of which are incorporated herein by reference.

A first embodiment of the invention encompasses a method of preparing a sulfinamide or sulfoxide, which comprises contacting a compound of Formula 1:

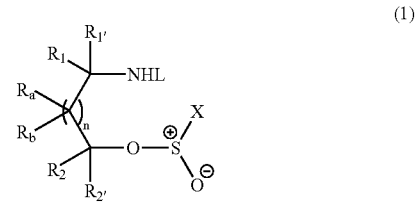

(1)

wherein n is 0 to 3; L is $CO_mR_3$ or $SO_mR_3$, wherein m is 0 to 3; $R_1$ and $R_2$ together form a cyclic structure (e.g., substituted or unsubstituted heterocycle or aryl) or each of $R_1$ and $R_2$ is independently substituted or unsubstituted alkyl, substituted or unsubstituted aralkyl, substituted or unsubstituted heteroalkyl, substituted or unsubstituted aryl, substituted or unsubstituted heterocycle; $R_{1'}$ and $R_{2'}$ together form a cyclic structure or each of $R_{1'}$ and $R_{2'}$ is independently hydrogen, substituted or unsubstituted alkyl, substituted or unsubstituted aralkyl, substituted or unsubstituted heteroalkyl, substituted or unsubstituted aryl, or substituted or unsubstituted heterocycle; $R_a$ and $R_b$ together form a cyclic structure or each of $R_a$ and $R_b$ is independently hydrogen, substituted or unsubstituted alkyl, substituted or unsubstituted aralkyl, substituted or unsubstituted heteroalkyl, substituted or unsubstituted aryl, or substituted or unsubstituted heterocycle; and each of $R_3$ and X is independently a polymer bound alkyl, aryl or heteroalkyl, substituted or unsubstituted alkyl, substituted or unsubstituted aralkyl, substituted or unsubstituted heteroalkyl, substituted or unsubstituted aryl, substituted or unsubstituted ether, substituted or unsubstituted ester, substituted or unsubstituted ketone, substituted or unsubstituted phosphonate, substituted or unsubstituted phosphonic acid ester, substituted or unsubstituted phosphinoyl (e.g., —P(=O)(R$_1$)$_3$; wherein R$_1$ is defined above), substituted or unsubstituted sulfide, substituted or unsubstituted sulfone, substituted or unsubstituted sulfinyl imine (e.g., —S(=O)(=NR$_1$)—R$_2$ wherein R$_1$ and R$_2$ are defined above), substituted or unsubstituted heterocycle, or —NR$_4$R$_5$, wherein R$_4$ and R$_5$ together with the nitrogen atom to which they are attached form a heterocycle or each of R$_4$ and R$_5$ is independently hydrogen, substituted or unsubstituted alkyl, substituted or unsubstituted heteroalkyl, substituted or unsubstituted aralkyl, substituted or unsubstituted aryl, substituted or unsubstituted ether, substituted or unsubstituted sulfide, or substituted or unsubstituted heterocycle;

with a compound of the formula MY, wherein M is a metal or metal complex capable of transferring Y to the positively charged sulfur atom of the compound of Formula 1 and Y is independently substituted or unsubstituted alkyl, substituted or unsubstituted aralkyl, substituted or unsubstituted heteroalkyl, substituted or unsubstituted aryl, substituted or unsubstituted ether, substituted or unsubstituted ester, substituted or unsubstituted ketone, substituted or unsubstituted phosphonate, substituted or unsubstituted phosphonic acid ester, substituted or unsubstituted phosphinoyl, substituted or unsubstituted sulfide, substituted or unsubstituted sulfone, substituted or unsubstituted sulfinyl imine, substituted or unsubstituted heterocycle, or is of the formula —NR$_6$R$_7$, wherein R$_6$ and R$_7$ together with the nitrogen atom to which they are attached form a heterocycle or each of R$_6$ and R$_7$ is independently a polymer bound alkyl, aryl or heteroalkyl; hydrogen; substituted or unsubstituted alkyl; substituted or unsubstituted aralkyl; substituted or unsubstituted heteroalkyl; substituted or unsubstituted aryl; substituted or unsubstituted ether; substituted or unsubstituted ester; substituted or unsubstituted ketone; substituted or unsubstituted phosphonate; substituted or unsubstituted phosphonic acid ester; substituted or unsubstituted phosphinoyl; substituted or unsubstituted sulfide; substituted or unsubstituted sulfone; substituted or unsubstituted sulfinyl imine; substituted or unsubstituted heterocycle; under conditions suitable for the formation of a compound of Formula 2:

(2)

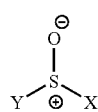

wherein X and Y are defined above.

In a preferred method of this embodiment, the compound(s) of Formula 1 and/or Formula 2 is/are stereomerically pure.

In another preferred embodiment, the compounds of Formula 1 have the following structures:

1A

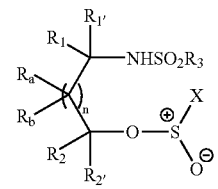

1B

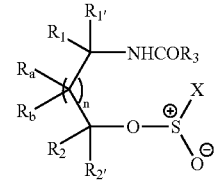

In another method of this embodiment, M of the formula MY is Al, Ba, Li, Na, K, Mg, Mn, Zn, Cd, In, or Cu; in another method, M is of the formula CdZ, BaZ, MgZ, ZnZ, AlZ$_2$, MnZ, InZ, or CuZ, wherein Z is Cl, Br, I, aryl, aralkyl, or heterocycle.

In another method, the compound of Formula 1 is prepared by contacting a compound of Formula 3:

(3)

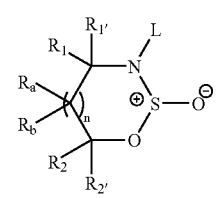

wherein n is 0 to 3; L is CO$_m$R$_3$ or SO$_m$R$_3$, wherein m is 0 to 3; and R$_1$, R$_2$, R$_{1'}$, R$_{2'}$, and R$_3$ are defined above;

with a compound of the formula M'X, wherein M' is a metal or metal complex capable of transferring X to the positively charged sulfur atom of the compound of Formula 3 and X is defined above.

In a preferred embodiment, the compounds of Formula 3 have the following structures:

3A

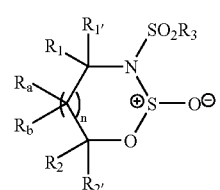

3B

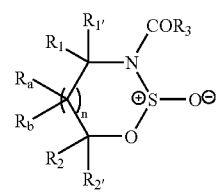

In a preferred method of this embodiment, M' of the formula M'X is Al, Ba, Li, Na, K, Mg, Mn, Zn, Cd, In, or Cu; in another method, M' is of the formula CdZ', BaZ', MgZ', ZnlZ', AlZ'$_2$, MnZ', InZ', or CuZ', wherein Z' is Cl, Br, I, aryl, aralkyl, or heterocycle or a combination with a Lewis acid, such as, but not limited to, Ti(OPr)$_4$ or Ti(OR$_1$)$_3$Cl, where R$_1$ is defined above.

In another preferred method of this embodiment, X is tert-butyl, trialkylmethyl, triheteroalkylmethyl, triarylmethyl, triheteroaryhnethyl, triheterocyclemethyl, aryl, heterocyclic, heteroaryl, alkyltrialkyl, alkylheteroalkylmethyl, diaryalkylmethyl, adamantyl, dialkyladamantyl, trialkylaryl, triethylmethyl, dimethylethyl, trimethylphenyl, trialkylphenyl, triisopropylphenyl, polymer bound alkyl or aryl or is of Formula 4: or is of Formula 4:

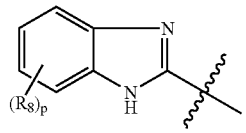

(4)

or a salt thereof, wherein each R$_8$ is independently substituted or unsubstituted alkyl, substituted or unsubstituted aralkyl, substituted or unsubstituted heteroalkyl, substituted or unsubstituted aryl, substituted or unsubstituted ether, substituted or unsubstituted sulfide, substituted or unsubstituted heterocycle, a primary, secondary, or tertiary amine, or a halogen atom; and p is an integer of 0 to 4; or is of Formula 5:

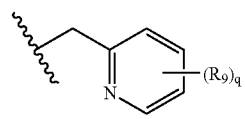

(5)

wherein each R$_9$ is independently substituted or unsubstituted alkyl, substituted or unsubstituted heteroalkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and q is an integer of 0 to 4. Preferably, q is 2 or 3.

If X is of Formula 4, p is preferably 0 or 1. If p is 1, R$_8$ is preferably —OCH$_3$ or —OCHF$_2$. If X is of Formula 5 and q is 2, each R$_9$ is preferably —CH$_3$, —OCH$_3$, —OCH$_2$CF$_3$, or —OC$_5$H$_{11}$; if q is 3, R$_9$ is preferably —CH$_3$ or —OCH$_3$.

In another preferred method of this embodiment, Y is —NR$_6$R$_7$ or is of Formula 4 or Formula 5. If Y is of Formula 4, p is preferably 0 or 1. If p is 1, R$_8$ is preferably —OCH$_3$ or —OCHF$_2$. If Y is of Formula 5 and q is 2, each R$_9$ is preferably —CH$_3$, —OCH$_3$, —OCH$_2$CF$_3$, or —OC$_5$H$_{11}$; if q is 3, R$_9$ is preferably —CH$_3$ or —OCH$_3$.

In another preferred method of this embodiment, R$_1$ is aryl or aklyl. In a more preferred method, R$_1$ is methyl.

In another preferred method of this embodiment, R$_2$ is aryl or alkyl. In a more preferred method, R$_2$ is phenyl.

In another preferred method of this embodiment, R$_3$ is a substituted or unsubstituted heteroalkyl, substituted or unsubstituted lower alkyl (e.g., halogenated phenyl, 3-methylphenyl, 4-methylphenyl, 1,3,5-trimethylphenyl, (tert-butyl)phenyl, 2-mesityl, tolyl, or 1,3,5-triisopropylphenyl), or aryl (e.g., phenyl and biphenyl). In a more preferred method, R$_3$ is 2-mesityl, tolyl, tri-isopropyl, or a polymer bound aryl or alkyl.

In a preferred method of this embodiment, the compound of Formula 1 is stereomerically pure and has one of the following stereochemistries:

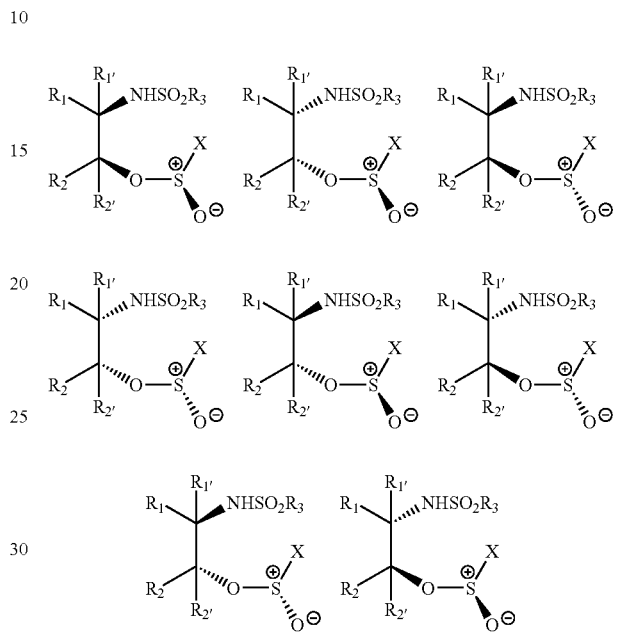

In another preferred method of this embodiment, the compound of Formula 1 has one of the following structures:

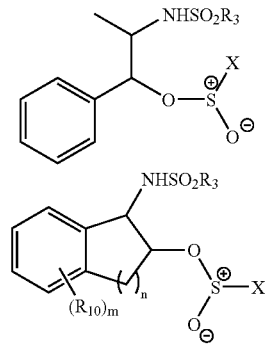

wherein X and R$_3$ are each defined above and each R$_{10}$ is independently substituted or unsubstituted alkyl, substituted or unsubstituted aralkyl, substituted or unsubstituted aryl, substituted or unsubstituted ether, substituted or unsubstituted sulfide, a primary, secondary, or tertiary amine, a heterocycle, or a halogen atom; n is an integer of 1 to 4; and m is an integer of 0 to 4. In a preferred method, n is 1 and m is 0, 1, or 2, and wherein R$_3$ is tert-butyl, trialkylmethyl, triheteroalkylmethyl, triarylmethyl, triheteroarylmethyl, triheterocyclemethyl, aryl, heterocyclic, heteroaryl, alkyltrialkyl, alkylheteroalkylmethyl, diaryalkylmethyl, adamantyl, dialkyladamantyl, trialkylaryl, triethylmethyl, dimethylethyl, trimethylphenyl, trialkylphenyl, triisopropylphenyl, polymer bound alkyl or aryl or is of Formula 4:

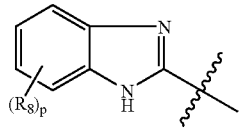

(4)

or a salt thereof, wherein each $R_8$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and p is an integer of 0 to 4; or is of Formula 5:

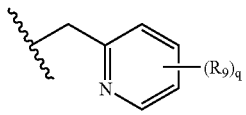

(5)

wherein each $R_9$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and q is an integer of 0 to 4. In a preferred method, the compound of Formula 6 or 7 is stereomerically pure.

In a preferred method of this embodiment, the compound of Formula 2 is of Formula 8, stereoisomers of which are shown below:

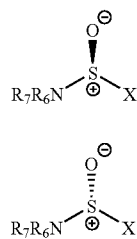

8(S)

8(R)

In a particularly preferred method of this embodiment, X is phenyl, 4-methylphenyl, tert-butyl, adamantyl, trimethylphenyl, pyridyl, or trialkylmethyl, triisopropylphenyl, trialkyl phenyl, tetraacylphenyl, or pentaalkylphenyl, triheteroalkylmethyl, triarylmethyl, triheteroarylmethyl, triheterocyclemethyl, aryl, heterocyclic, heteroaryl, alkyltrialkyl, alkylheteroalkylmethyl, diarylalkylmethyl, dialkyladamantyl, trialkylaryl, triethylmethyl, dimethylethyl, trialkylphenyl, triisopropylphenyl, polymer bound alkyl or aryl or is of Formula 4:

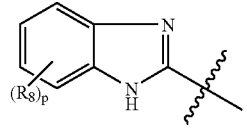

(4)

or a salt thereof, wherein each $R_8$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and p is an integer of 0 to 4; or is of Formula 5:

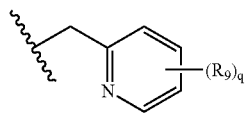

(5)

wherein each $R_9$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and q is an integer of 0 to 4. In another preferred method, at least one of $R_6$ and $R_7$ is hydrogen. In yet another preferred method, $R_6$ and $R_7$ are both hydrogen.

In another preferred method of this embodiment, the compound of Formula 3 has one of the following stereochemistries:

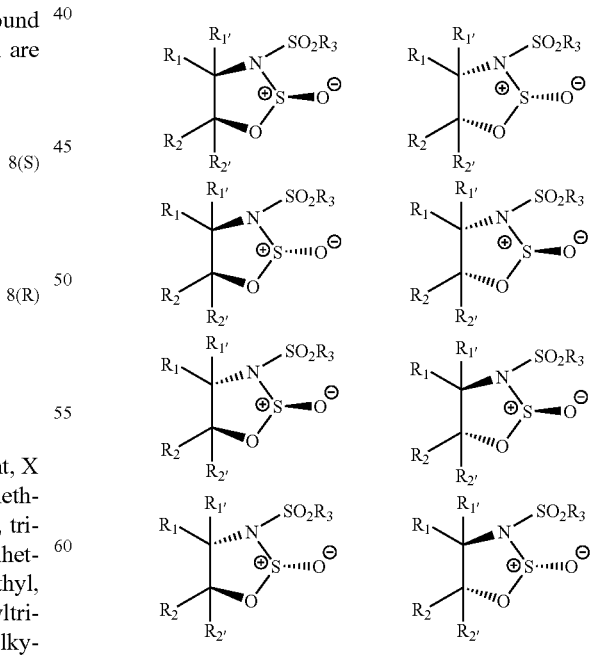

In a particularly preferred method of this embodiment, the compound of Formula 3 has one of the following structures:

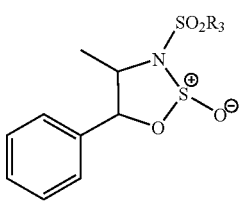

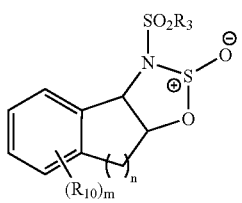

wherein $R_3$, $R_{10}$, m, and n are defined herein.

With regard to compound 10, when n is 1, the stereochemistry of the compound is preferably cis, two isomers of which are shown below:

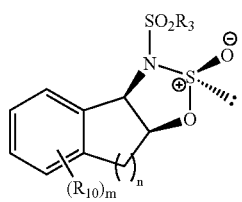

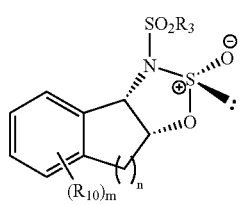

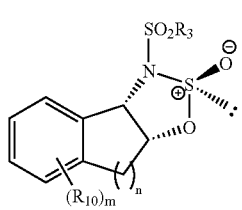

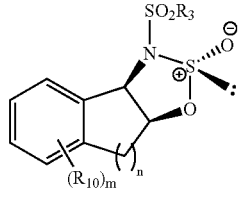

A specific method of this embodiment is a method of preparing pantoprazole, or a derivative, prodrug, salt, solvate, clathrate, or stereomerically pure form thereof, which comprises contacting a compound of Formula 11:

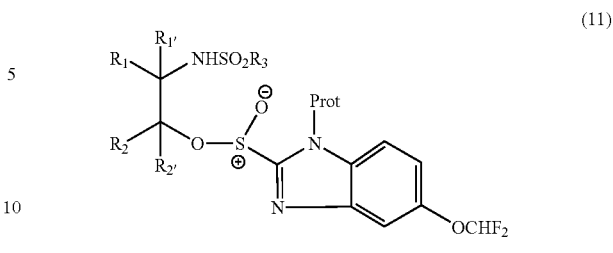

wherein $R_1$, $R_2$, $R_{1'}$, and $R_{2'}$ are defined herein, and Prot is a protecting group (e.g., an aminal or sulfanamide), with a compound of Formula 12:

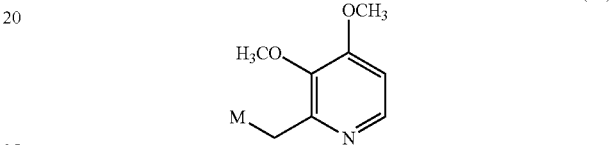

wherein M is defined herein, under conditions suitable for the formation of a compound of Formula 13:

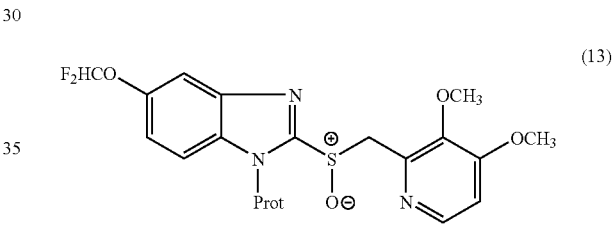

and optionally contacting the compound of Formula 13 with a reagent capable of replacing Prot with a hydrogen atom or a cation (e.g., $Na^+$ or $K^+$). Suitable reagents include, but are not limited to NaOH, KOH, or a mild acid followed by NaH or KH.

In a preferred method, the compound of Formula 11 is prepared by contacting a compound of Formula 3 with a compound of Formula 14:

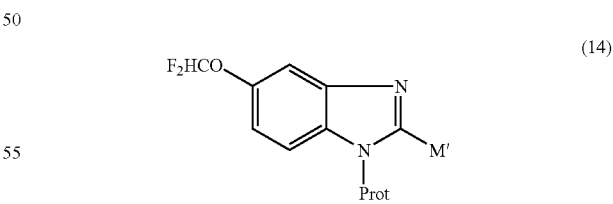

wherein M' is defined herein, under conditions sufficient for the formation of the compound of Formula 11.

In another preferred method, the compounds of formulas 11 and 13 are enantiomerically pure.

Another specific method of this embodiment is a method of preparing lansoprazole, or a derivative, prodrug, salt, solvate, clathrate, or stereomerically pure form thereof, which comprises contacting a compound of Formula 15:

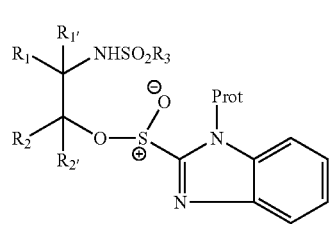

(15)

wherein $R_1$, $R_2$, $R_{1'}$, $R_{2'}$, and Prot are defined herein, with a compound of Formula 16:

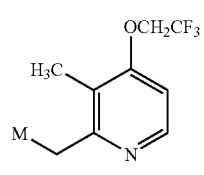

(16)

wherein M is defined herein, under conditions suitable for the formation of a compound of Formula 17:

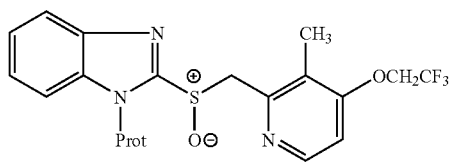

(17)

and optionally contacting the compound of Formula 17 with a reagent capable of replacing Prot with a hydrogen atom or a cation.

In a preferred method, the compound of Formula 15 is prepared by contacting a compound of Formula 3 with a compound of Formula 18:

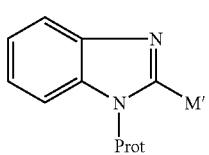

(18)

wherein M' is defined herein, under conditions sufficient for the formation of the compound of Formula 15.

In another preferred method, the compounds of formulas 15 and 17 are enantiomerically pure.

Another specific method of this embodiment is a method of preparing omeprazole, or a derivative, prodrug, salt, solvate, clathrate, or stereomerically pure form thereof, which comprises contacting a compound of Formula 19:

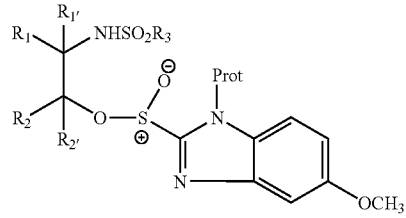

(19)

wherein $R_1$, $R_2$, $R_{1'}$, $R_{2'}$, and Prot are defined herein, with a compound of Formula 20:

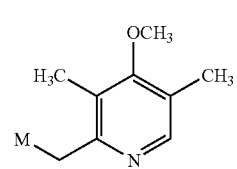

(20)

wherein M is defined herein, under conditions suitable for the formation of a compound of Formula 21:

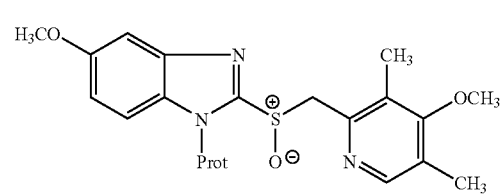

(21)

and optionally contacting the compound of Formula 21 with a reagent capable of replacing Prot with a hydrogen atom or a cation.

In a preferred method, the compound of Formula 19 is prepared by contacting a compound of Formula 3 with a compound of Formula 22:

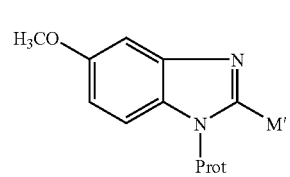

(22)

wherein M' is defined herein, under conditions sufficient for the formation of the compound of Formula 19.

In another preferred method, the compounds of formulas 19 and 21 are enantiomerically pure.

Still another specific method of this embodiment is a method of preparing rabeprazole, or a derivative, prodrug, salt, solvate, clathrate, or stereomerically pure form thereof, which comprises contacting a compound of Formula 15:

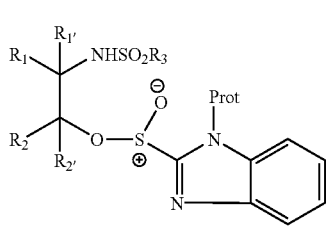

(15)

wherein $R_1$, $R_2$, $R_{1'}$, $R_{2'}$, and Prot are defined herein, with a compound of Formula 23:

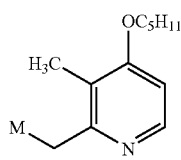

(23)

wherein M is defined herein, under conditions suitable for the formation of a compound of Formula 24:

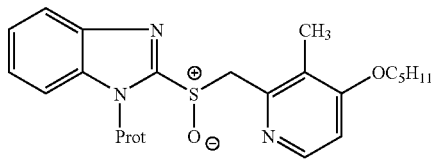

(24)

and optionally contacting the compound of Formula 24 with a reagent capable of replacing Prot with a hydrogen atom or a cation.

In a preferred method, the compound of Formula 15 is prepared by contacting a compound of Formula 3 with a compound of Formula 18:

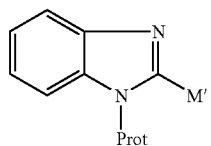

(18)

wherein M' is defined herein, under conditions sufficient for the formation of the compound of Formula 23.

In another preferred method, the compounds of formulas 23 and 25 are enantiomerically pure.

A second embodiment of the invention encompasses various compounds that are particularly useful for the preparation of sulfinamides and sulfoxides. For example, the invention encompasses compounds of Formula 7:

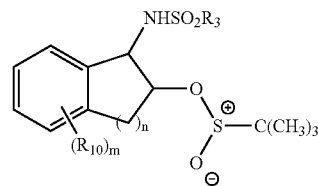

(7)

and salts, solvates, clathrates, and stereomerically pure forms thereof, wherein $R_3$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, or —$NR_4R_5$, wherein $R_4$ and $R_5$ together with the nitrogen atom to which they are attached form a heterocycle or each of $R_4$ and $R_5$ is independently hydrogen, is independently substituted or unsubstituted alkyl, substituted or unsubstituted aralkyl, substituted or unsubstituted aryl, substituted or unsubstituted ether, substituted or unsubstituted sulfide, or substituted or unsubstituted heterocycle; each $R_{10}$ is independently substituted or unsubstituted alkyl, substituted or unsubstituted aralkyl, substituted or unsubstituted aryl, substituted or unsubstituted ether, substituted or unsubstituted sulfide, a primary, secondary, or tertiary amine, a heterocycle, or a halogen atom; n is an integer of 1 to 4; and m is an integer of 0 to 4.

In preferred compounds of Formula 7, $R_3$ is a substituted or unsubstituted lower alkyl, substituted or unsubstituted aralkyl (e.g., halogenated phenyl, 3-methylphenyl, 2-methylphenyl, 2-mesityl, tolyl, 4-(tert-butyl)phenyl, or 2,4,6-triisopropylphenyl), or aryl (e.g., phenyl and biphenyl). In more preferred compounds, $R_3$ is 2-mesityl or tolyl.

In other preferred compounds of Formula 7, each $R_{10}$ is independently substituted or unsubstituted alkyl, substituted or unsubstituted aralkyl, or substituted or unsubstituted aryl. In more preferred compounds of Formula 7, each $R_{10}$ is independently alkyl, aralkyl, or aryl.

In preferred compounds of Formula 7, n is 1 and m is 0, 1, or 2.

Preferred compounds of Formula 7 are stereomerically pure.

The invention further encompasses compounds of Formula 25:

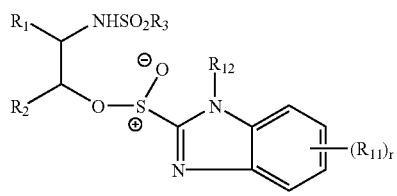

(25)

and salts, solvates, clathrates, and stereomerically pure forms thereof, wherein $R_1$ and $R_2$ together form a cyclic structure (e.g., substituted or unsubstituted heterocycle or aryl) or each of $R_1$ and $R_2$ is independently substituted or unsubstituted alkyl, substituted or unsubstituted aralkyl, substituted or unsubstituted aryl, or substituted or unsubstituted heterocycle; $R_3$ is substituted or unsubstituted alkyl, substituted or unsubstituted aralkyl, substituted or unsubstituted aryl, substituted or unsubstituted ether, substituted or unsubstituted sulfide, substituted or unsubstituted heterocycle, or —$NR_4R_5$, wherein $R_4$ and $R_5$ together with the nitrogen atom to which they are attached form a heterocycle or each of $R_4$ and $R_4$ is independently hydrogen, substituted or unsubstituted alkyl, substituted or unsubstituted aralkyl, substituted or unsubstituted aryl, substituted or unsubstituted ether, substituted or unsubstituted sulfide, or substituted or unsubstituted heterocycle; each $R_{11}$ is independently substituted or unsubstituted alkyl, substituted or unsubstituted aralkyl, substituted or unsubstituted aryl, substituted or unsubstituted ether, substituted or unsubstituted sulfide, a primary, secondary, or tertiary amine, a heterocycle, or a halogen atom; $R_{12}$ is substituted or unsubstituted alkyl, substituted or unsubstituted aralkyl, substituted or unsubstituted aryl, substituted or unsubstituted ether, substituted or unsubstituted sulfide, or substituted or unsubstituted heterocycle, or is a sulfoxide; and r is an integer from 0 to 4.

In preferred compounds of Formula 25, n is 1, m is 0, 1, or 2, and r is 2 or 3.

In additional preferred compounds of Formula 25, $R_1$ is phenyl or lower alkyl. In a particular compound, $R_1$ is methyl.

In additional preferred compounds of Formula 25, $R_2$ is phenyl or lower alkyl. In a particular compound, $R_2$ is phenyl.

In additional preferred compounds of Formula 25, $R_3$ is a substituted or unsubstituted lower alkyl, substituted or unsubstituted aralkyl (e.g., halogenated phenyl, 3-methylphenyl, 4-methylphenyl, 1,3,5-trimethylphenyl, (tert-butyl)phenyl, 2-mesityl, tolyl, or 1,3,5-triisopropylphenyl), or aryl (e.g., phenyl and biphenyl). In a particular compound, $R_3$ is 2-mesityl or tolyl.

Specific preferred compounds of Formula 25 are those of Formula 26:

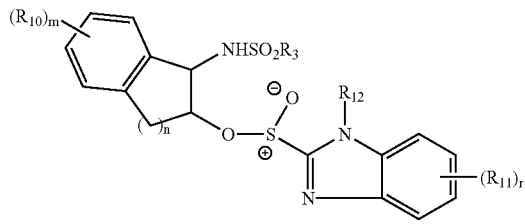

(26)

and salts, solvates, clathrates, and stereomerically pure forms thereof, wherein each $R_{11}$ is independently substituted or unsubstituted alkyl, substituted or unsubstituted aralkyl, substituted or unsubstituted aryl, substituted or unsubstituted ether, substituted or unsubstituted sulfide, a primary, secondary, or tertiary amine, a heterocycle, or a halogen atom; $R_{12}$ is substituted or unsubstituted alkyl, substituted or unsubstituted aralkyl, substituted or unsubstituted aryl, substituted or unsubstituted ether, substituted or unsubstituted sulfide, or substituted or unsubstituted heterocycle, or is a sulfoxide; and r is an integer from 0 to 4.

In preferred compounds of Formula 26, $R_{12}$ is a protecting group.

In preferred compounds of Formula 26, each $R_{11}$ is independently substituted or unsubstituted alkyl or substituted or unsubstituted ether.

In preferred compounds of Formula 26, n is 1, m is 0, 1, or 2, and r is 2 or 3.

The invention further encompasses compounds of Formula 9:

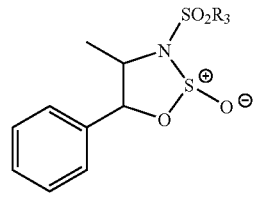

and salts, solvates, clathrates, and stereomerically pure forms thereof, wherein $R_3$ is substituted or unsubstituted alkyl, substituted or unsubstituted aralkyl, substituted or unsubstituted aryl, substituted or unsubstituted ether, substituted or unsubstituted sulfide, substituted or unsubstituted heterocycle, polymer bound alkyl or aryl, or —$NR_4R_5$, wherein $R_4$ and $R_5$ together with the nitrogen atom to which they are attached form a heterocycle or each of $R_4$ and $R_5$ is independently hydrogen, substituted or unsubstituted alkyl, substituted or unsubstituted aralkyl, substituted or unsubstituted aryl, substituted or unsubstituted ether, substituted or unsubstituted sulfide, or substituted or unsubstituted heterocycle.

In preferred compounds of Formula 9, $R_3$ is a substituted or unsubstituted lower alkyl, substituted or unsubstituted aralkyl (e.g., halogenated phenyl, 3-methylphenyl, 2-methylphenyl, 2-mesityl, tolyl, 4-(tert-butyl)phenyl, or 2,4,6-triisopropylphenyl), or aryl (e.g., phenyl and biphenyl). In more preferred compounds, $R_3$ is 2-mesityl or tolyl.

Preferred compounds of Formula 9 are stereomerically pure.

The invention further encompasses compounds of Formula 10:

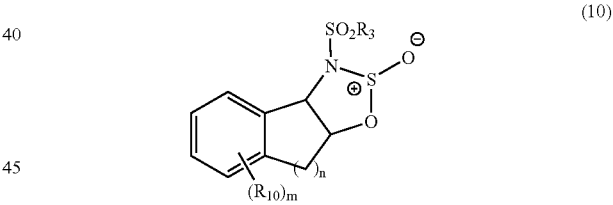

(10)

and salts, solvates, clathrates, and stereomerically pure forms thereof, wherein $R_3$ is substituted or unsubstituted alkyl, substituted or unsubstituted aralkyl, substituted or unsubstituted aryl, substituted or unsubstituted ether, substituted or unsubstituted sulfide, substituted or unsubstituted heterocycle, polymer bound alkyl or aryl, or —$NR_4R_5$, wherein $R_4$ and $R_5$ together with the nitrogen atom to which they are attached form a heterocycle or each of $R_4$ and $R_5$ is independently hydrogen, substituted or unsubstituted alkyl, substituted or unsubstituted aralkyl, substituted or unsubstituted aryl, substituted or unsubstituted ether, substituted or unsubstituted sulfide, or substituted or unsubstituted heterocycle; each $R_{10}$ is independently substituted or unsubstituted alkyl, substituted or unsubstituted aralkyl, substituted or unsubstituted aryl, a primary, secondary, or tertiary amine, or a halogen atom; n is an integer of 1 to 4; and m is an integer of 0 to 4.

In preferred compounds of Formula 10, $R_3$ is a substituted or unsubstituted lower alkyl, substituted or unsubstituted aralkyl (e.g., halogenated phenyl, 3-methylphenyl, 2-methylphenyl, 2-mesityl, tolyl, 4-(tert-butyl)phenyl, or 2,4,6-triisopropylphenyl), or aryl (e.g., phenyl and biphenyl). In more preferred compounds, $R_3$ is 2-mesityl or tolyl.

In other preferred compounds of Formula 10, n is 1 and m is 0, 1, or 2.

Preferred compounds of Formula 10 are stereomerically pure.

Also encompassed by the invention are compounds of Formula 56:

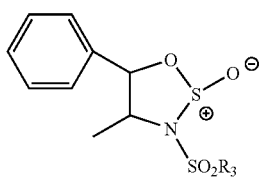
(56)

and salts, solvates, clathrates, and stereomerically pure forms thereof, wherein $R_3$ is substituted or unsubstituted alkyl, substituted or unsubstituted aralkyl, substituted or unsubstituted aryl, substituted or unsubstituted ether, substituted or unsubstituted sulfide, substituted or unsubstituted heterocycle, polymer bound alkyl or aryl, or —$NR_4R_5$, wherein $R_4$ and $R_5$ together with the nitrogen atom to which they are attached form a heterocycle or each of $R_4$ and $R_5$ is independently hydrogen, substituted or unsubstituted alkyl, substituted or unsubstituted aralkyl, substituted or unsubstituted aryl, substituted or unsubstituted ether, substituted or unsubstituted sulfide, or substituted or unsubstituted heterocycle.

In preferred compounds of Formula 56, $R_3$ is a substituted or unsubstituted lower alkyl, substituted or unsubstituted aralkyl (e.g., halogenated phenyl, 3-methylphenyl, 2-methylphenyl, 2-mesityl, tolyl, 4-(tert-butyl)phenyl, or 2,4,6-triisopropylphenyl), or aryl (e.g., phenyl and biphenyl). In more preferred compounds, $R_3$ is 2-mesityl or tolyl.

Preferred compounds of Formula 56 are stereomerically pure.

4.1. Preparation of Sulfinamides and Sulfoxides

In general, sulfinamides and sulfoxides are prepared according to this invention by contacting a compound of Formula 1:

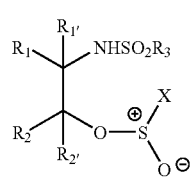
(1)

wherein $R_1$, $R_{1'}$, $R_2$, $R_{2'}$, $R_3$, and X are defined herein, with a reagent that will cleave the sulfur-oxygen bond to provide a compound of Formula 2:

(2)

In preferred methods of the invention, the compounds of formulas 1 and 2 are stereomerically pure.

A particular method of the invention is shown below in Scheme II:

Scheme II

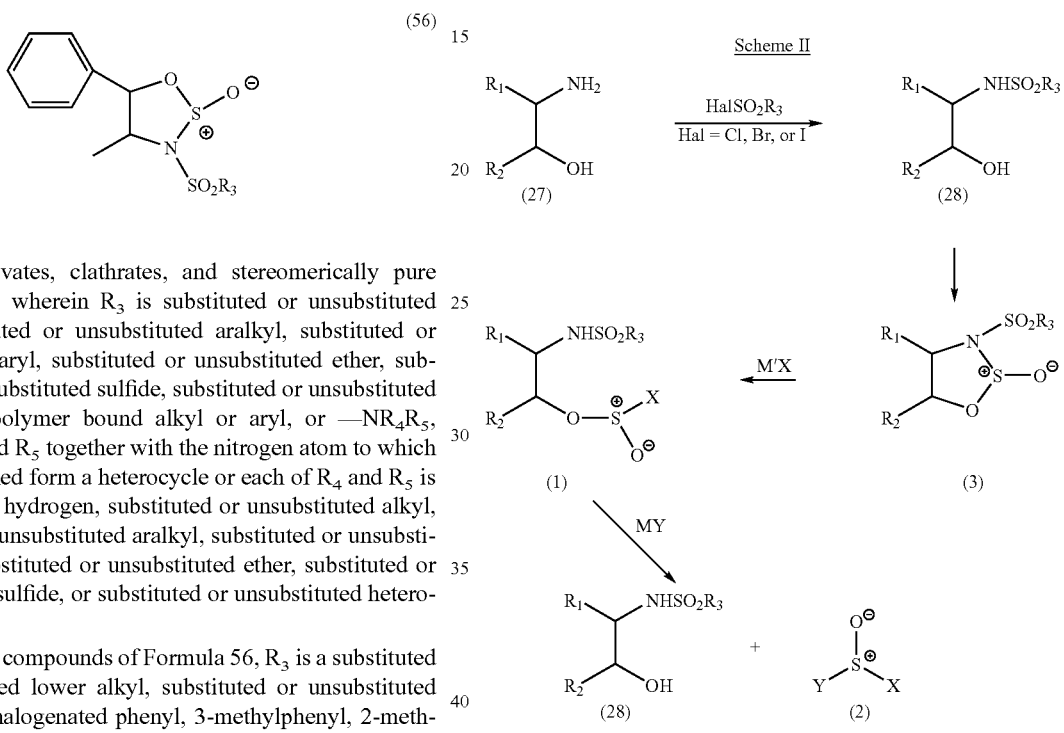

As shown in Scheme II, a compound of Formula 27 is contacted with a compound of the formula $HalSO_2R_3$, wherein Hal is halogen and $R_1$, $R_2$, and $R_3$ are defined herein, under conditions suitable for the formation of a compound of Formula 28. Examples of $HalSO_2R_3$ include, but are not limited to, p-toluenesulfonyl chloride and mesitylsulfonyl chloride. As those of skill in the art will recognize, the particular conditions sufficient for this reaction to occur will depend on the specific compounds being reacted. Suitable conditions will be readily apparent to the skilled chemist. In one example, triethylamine is used with a solvent such as, but not limited to, methylene chloride.

The compound of Formula 28 is then contacted with a reagent capable of forming a five-membered ring to provide compound 3. One example of such a reagent is $SOCl_2$ with a base in a suitable solvent. Examples of bases include, but are not limited to, trialkylamines (e.g., triethylamine), pyridine, imidazole, quinoline, and derivatives thereof. Examples of suitable solvents include, but are not limited to, THF, methyl-THF, $CH_2Cl_2$, $ClCH_2CH_2Cl$, toluene, chlorobenzene, dichlorobenzene, dioxanes, MTBE/THF, DME, and other solvent mixtures. Another example of a reagent that can be used to form the compound of Formula 3 is 2,4,6-collidine or a substituted pyridine or pyridine analogue in a solvent such as, but not limited to, THF.

The effects of various reagents and reaction conditions on the formation and stereochemistry of specific compounds of Formula 3 shown below, are provided in Table 1:

TABLE 1

(endo structure shown)

(exo structure shown)

| $R_3$ | $R_{10}'$ and $R_{10}''$ | n | Base | Endo:Exo (solvent at −45° C. unless otherwise indicated) |
|---|---|---|---|---|
| 4-methylphenyl | H | 1 | Triethylamine | 75:25 (THF) |
| " | " | 1 | Triethylamine | 62:38 (THF/CH$_2$Cl$_2$ 1:1) |
| " | " | 1 | Triethylamine | 87:13 (CH$_3$CN) |
| " | " | 1 | Triethylamine | 73:27 (EtOAc) |
| " | " | 1 | Imidazole | 70:30 (THF) |
| " | " | 1 | 1-Methylimidazole | 75:25 (THF) |
| " | " | 1 | Pyridine | 75:25 (THF) |
| " | " | 1 | 2,6-Lutidine | 85:15 (THF) |
| " | " | 1 | 2,4,6-Collidine | 91:9 (THF) |
| " | " | 1 | 2,6-Di-t-Butylpyridine | 3:97 (THF) |
| " | " | 1 | 4-Me-2,6-t-Bu-pyridine | 20:80 (THF) (−20° C.) |
| " | " | 1 | 4-t-Butylpyridiene | 84.3:15.7 (THF) |
| " | " | 1 | 2,6-Dimethoxypyridine | 15.8:84.2 (CH$_2$Cl$_2$, 0° C.) |
| " | " | 1 | Quinaldine | 87:13 (THF) |
| " | " | 1 | Lepidine | 88:12 (THF) |
| " | CH$_3$ | 1 | Pyridine | 97:3 (THF) |
| " | H | 2 | Pyridine | 97:3 (THF) |
| " | " | 1 | 4-Picoline | 78:22 (THF) |
| 2-mesityl | H | 1 | Triethylamine | 85:15 (THF) |
| " | " | 1 | Triisopropylamine | 66.7:33.3 (THF) |
| " | " | 1 | Diethylaniline | 2:98 (CH$_2$Cl$_2$, −15° C.) |
| " | " | 1 | Diethylaniline | 37:63 (THF, −20° C.) |
| " | " | 1 | Triphenyamine | No reaction |
| " | " | 1 | Imidazole | 82:18 (THF) |
| " | " | 1 | 2-Methylimidazole | 85.7:14.3 (THF) |
| " | " | 1 | 2-Ethylimidazole | 66:33 |
| " | " | 1 | Pyridine | 90:10 (THF) |
| " | " | 1 | 2-Phenylpyridine | 83:17 (THF) |
| " | " | 1 | 2,4,6-Collidine | 93:7 (THF) |
| " | " | 1 | 2,6-Dimethoxypyridine | 2:98 (CH$_2$Cl$_2$, −15° C.) |
| " | " | 1 | 2,6-Dimethoxypyridine | 75:25 (THF, −45° C. - r.t) |
| " | " | 1 | Lepidine | 94:6 (THF) |
| 2,4,6-triisopropyl phenyl | H | 1 | Triethylamine | 87:13 (THF) |
| 2,4,6-triisopropyl phenyl | " | 1 | 2,4,6-Collidine | 95:5 (THF) |
| 4-t-butylphenyl | H | 1 | Triethylamine | 80:20 (THF) |
| " | " | 1 | Triethylamine | 40:60 (CH$_2$Cl$_2$) |
| 4-methylphenyl | CH$_3$ | 1 | Triethylamine | 85.7:14.3 (CH$_2$Cl$_2$) |

As shown in Scheme II, the ring of compound 3 is selectively opened by contacting it with an organometallic reagent to provide a compound of Formula 1. Examples of organometallic reagents include, but are not limited to, those of the formula M'X, wherein M' of the formula M'X is Al, Ba, Li, Na, K, Mg, Mn, Zn, Cd, In, Cu or is of the formula CdZ', BaZ', MgZ', ZnZ', AlZ'$_2$, MnZ', InZ', CuZ', Ti(OR$_1$)$_3$ Z', or Ti(OR$_1$)$_4$ wherein Z' is Cl, Br, I, aryl, aralkyl, or heterocycle, wherein R, is defined herein.

The sulfur-oxygen bond of the compound of Formula 1 is then cleaved by contacting it with a compound of formula MY to provide the desired sulfinamide or sulfoxide of Formula 2. MY can be the same or different from MZ: M is a metal such as Al, Ba, Li, Na, K, Mg, Mn, Zn, Cd, In, Cu or is of the formula CdZ, BaZ, MgZ, ZnZ, AlZ$_2$, MnZ, InZ, or CuZ, Ti(OR$_1$)$_3$Z, or Ti(OR$_1$)$_4$ wherein Z is Cl, Br, I, aryl, aralkyl, or heterocycle, wherein R$_1$ is defined herein.

Depending on the actual compound of formula MY, this final reaction of Scheme II can provide a variety of different sulfoxides and sulfinamides, and stereomerically pure sulfoxides and sulfinamides in particular. For example, when MY is NH$_2$Li/NH$_3$, this method can be used to provide stereomerically pure alkyl (e.g., tert-butyl), aryl (e.g., tolyl), heteroalkyl (e.g., tert-butyl amino), heterocyclic (e.g., tetrahydrofuryl), or heteroaryl (e.g., pyridyl) sulfinamide.

Specific methods of the invention, which can be used to prepare enantiomerically pure pantoprazole, lansoprazole, omeprazole, and rabeprazole, and pharmaceutically acceptable salts, solvates, clathrates, hydrates, prodrugs, and stereomerically pure forms thereof, are represented below in schemes III–VI, respectively. In each scheme, the stereochemistry of the compound of Formula 3 is different in order to emphasize that the stereochemistry of the final product can be varied by simply altering the corresponding stereochemistry of the starting material. As with all schemes disclosed herein, those shown below are provided by way of illustration, and are not to be construed as limiting the scope of the invention.

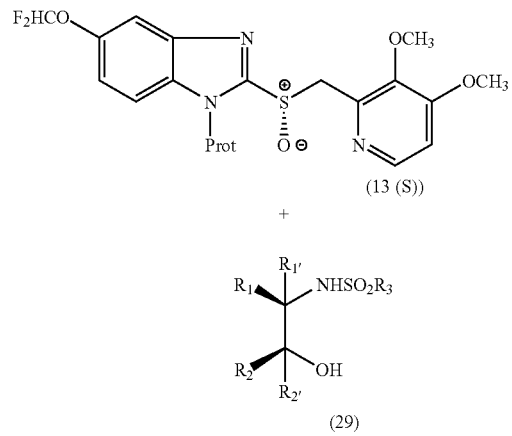

Scheme IV

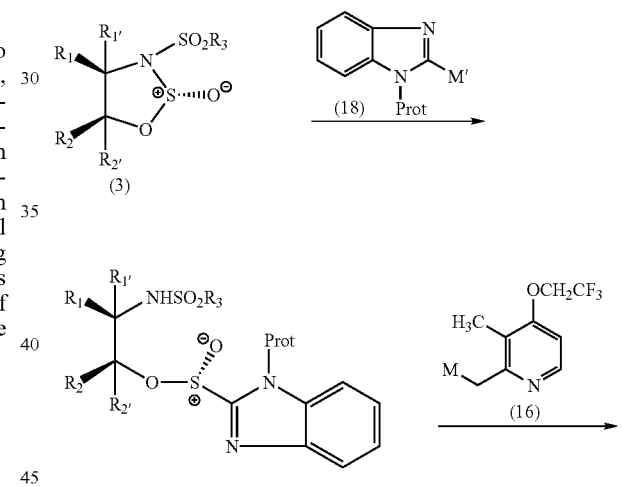

Scheme III

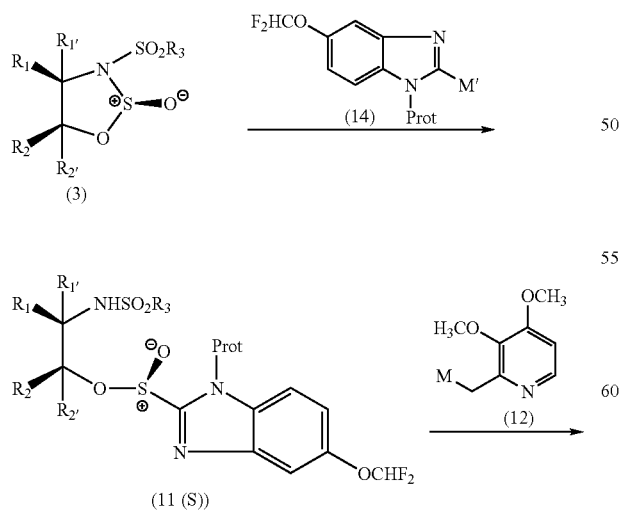

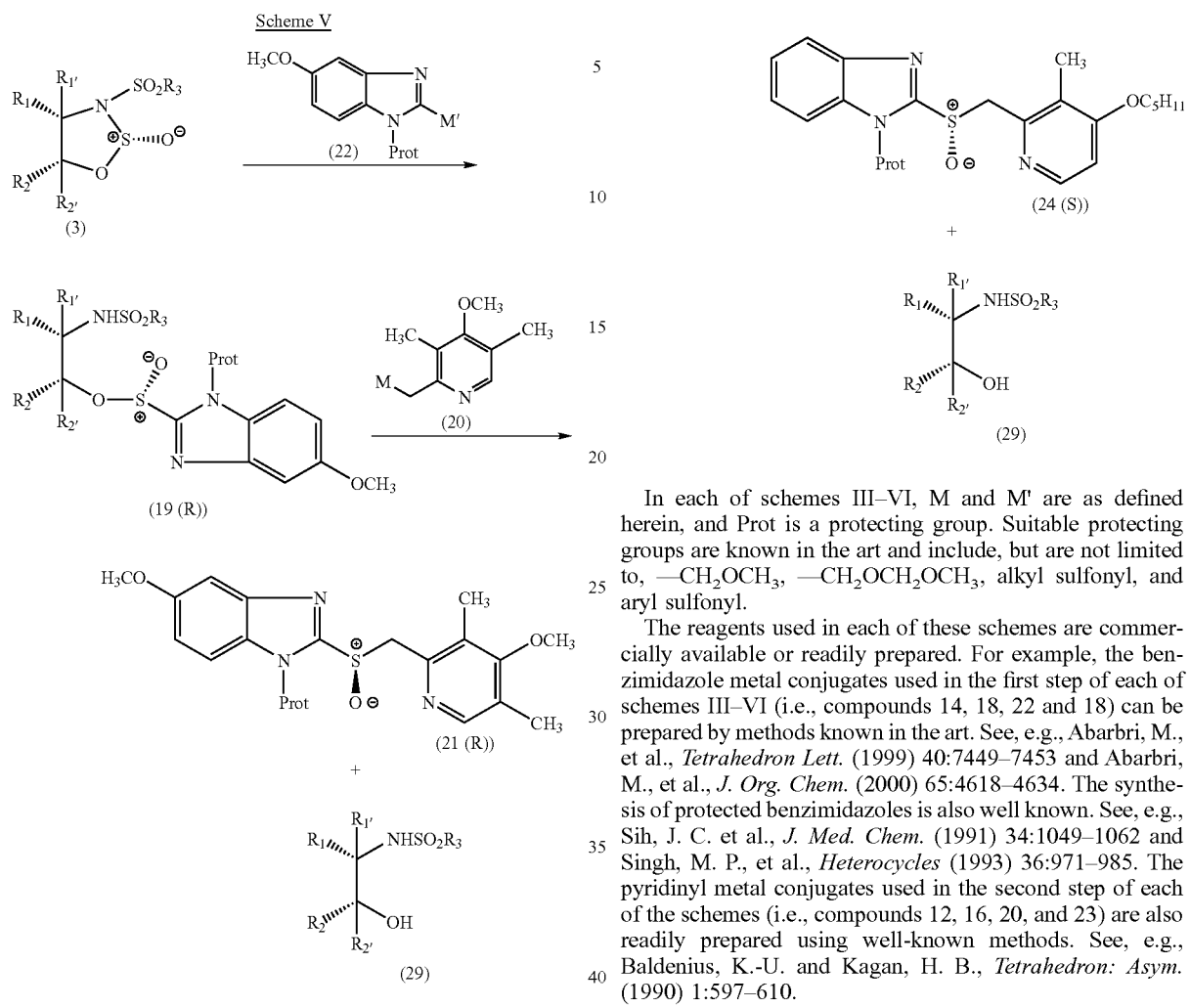

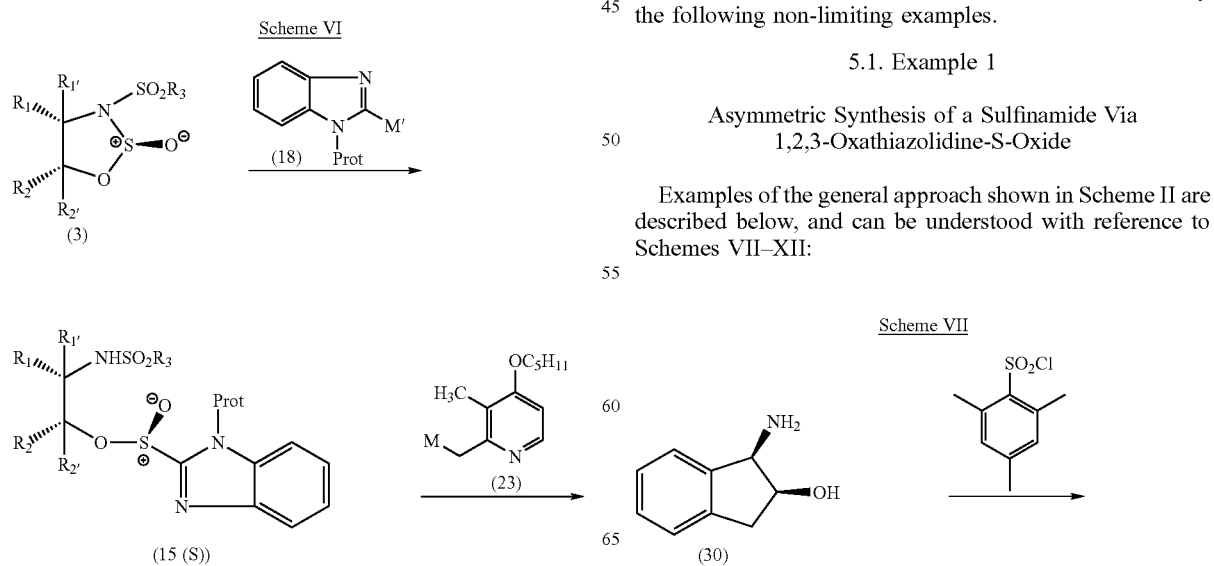

In each of schemes III–VI, M and M' are as defined herein, and Prot is a protecting group. Suitable protecting groups are known in the art and include, but are not limited to, —CH$_2$OCH$_3$, —CH$_2$OCH$_2$OCH$_3$, alkyl sulfonyl, and aryl sulfonyl.

The reagents used in each of these schemes are commercially available or readily prepared. For example, the benzimidazole metal conjugates used in the first step of each of schemes III–VI (i.e., compounds 14, 18, 22 and 18) can be prepared by methods known in the art. See, e.g., Abarbri, M., et al., *Tetrahedron Lett.* (1999) 40:7449–7453 and Abarbri, M., et al., *J. Org. Chem.* (2000) 65:4618–4634. The synthesis of protected benzimidazoles is also well known. See, e.g., Sih, J. C. et al., *J. Med. Chem.* (1991) 34:1049–1062 and Singh, M. P., et al., *Heterocycles* (1993) 36:971–985. The pyridinyl metal conjugates used in the second step of each of the schemes (i.e., compounds 12, 16, 20, and 23) are also readily prepared using well-known methods. See, e.g., Baldenius, K.-U. and Kagan, H. B., *Tetrahedron: Asym.* (1990) 1:597–610.

5. EXAMPLES

Certain embodiments of the invention are illustrated by the following non-limiting examples.

5.1. Example 1

Asymmetric Synthesis of a Sulfinamide Via 1,2,3-Oxathiazolidine-S-Oxide

Examples of the general approach shown in Scheme II are described below, and can be understood with reference to Schemes VII–XII:

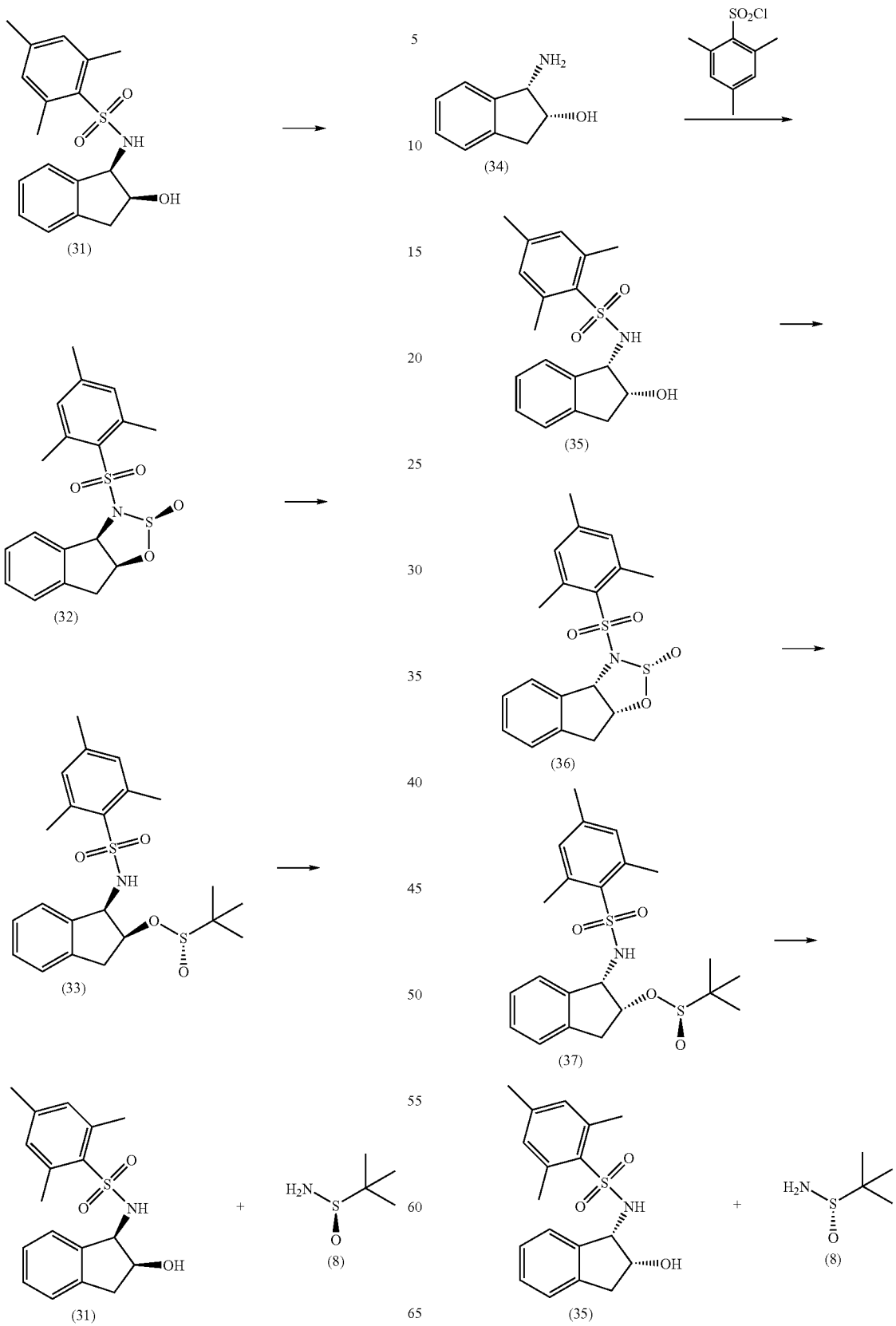

Scheme IX
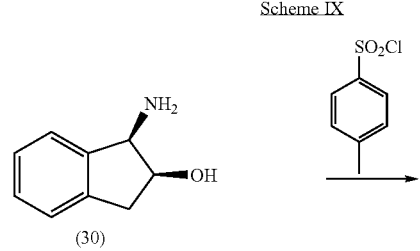
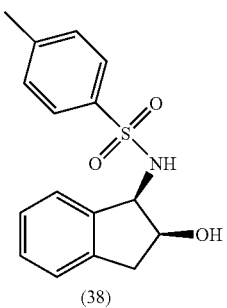
(38)
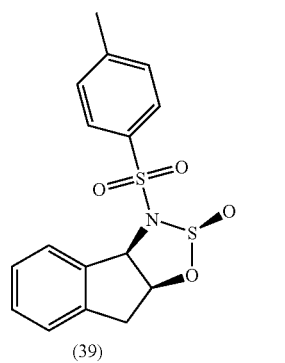
(39)
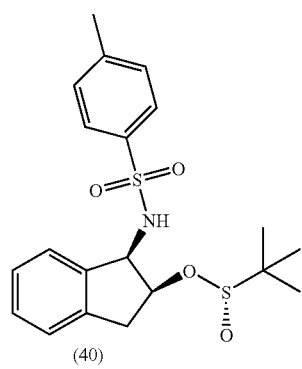
(40)
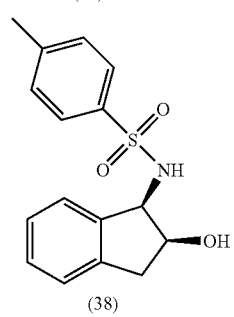
(38)
Scheme X
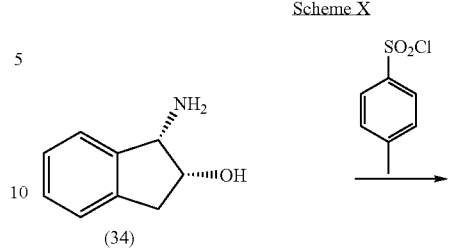
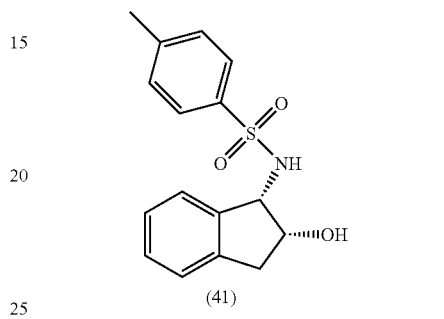
(41)
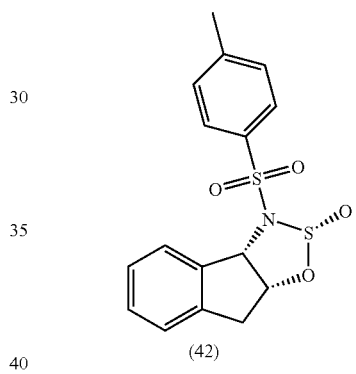
(42)
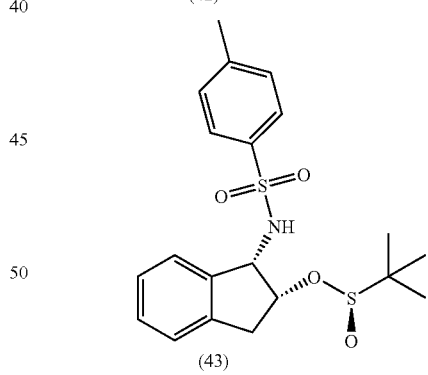
(43)
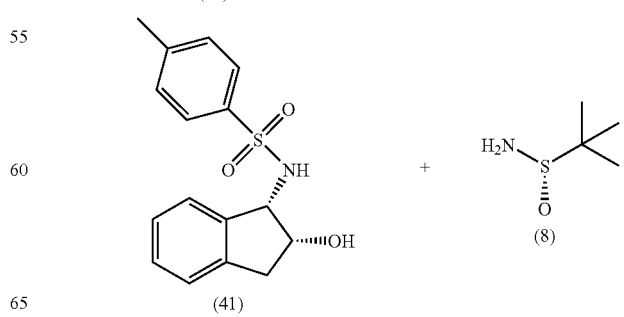
(41) + (8)

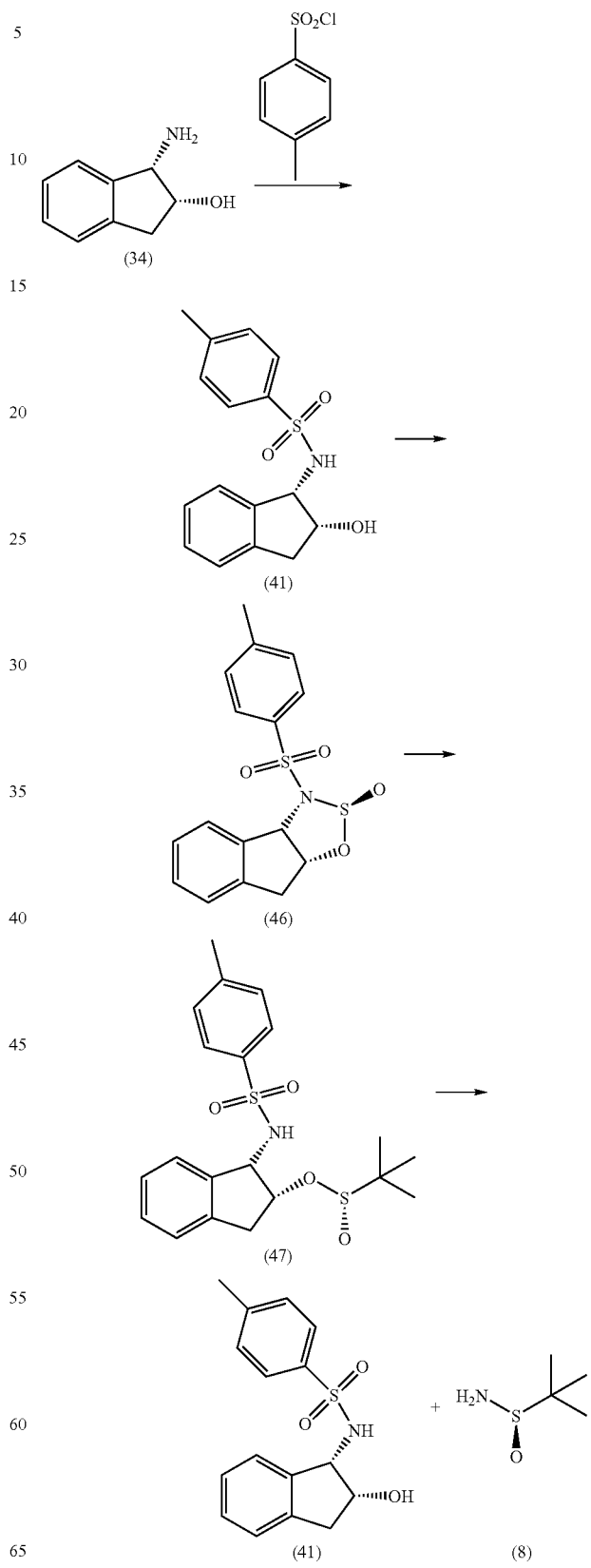

Preparation of (1R,2S)-1-amino-2-indanol-N-2,4,6-mesitylsulfonamide (31): To a 2 L mL three neck round-bottomed flask equipped with an overhead stirrer and temperature probe, was charged NaHCO$_3$ (42.2 g, 502 mmol), followed by 200 mL of water and the mixture was stirred for 15 min. EtOAc (500 mL), THF (100 mL), and aminoindanol (30) (50 g, 336 mmol) were added and the slurry was mixed for 5 minutes. 2-Mesitylenesulfonyl chloride (70.4 g, 322 mmol) was added in one portion, the reaction mixture was stirred vigorously for 5–6 hours, and the reaction was monitored by TLC for the disappearance of 2-mesitylenesulfonyl chloride. Stirring was stopped and the phases were allowed to separate. The organic phase was washed with water (200 mL), 1.5 M HCl (75 mL) and water (200 mL). Evaporation of the organic solvent to dryness provided a solid product which was treated with heptane (400 mL) and the mixture was stirred for 2 hours. The resulting slurry was filtered and the wet cake dried under reduced pressure to give 104 g (93%) of the title product. $^1$H NMR(300 MHz, CDCl$_3$): δ 2.30 (s, 3H), 2.68 (s, 6H), 2.81–3.04 (m, 3H), 4.22–4.32 (m, 1H), 4.48–4.58 (m, 1H), 5.58–5.61 (d, J=9.5 Hz, 1H), 6.95–7.24 (m, 6H). $^{13}$C NMR (CDCl$_3$): δ 21.3, 23.3, 39.6, 61.3, 73.2, 124.9, 125.6, 127.4, 128.7, 132.3, 134.1, 139.7, 139.8, 140.0, and 142.8. Alal. Calcd for C$_{18}$H$_{21}$NO$_3$S: C, 65.23; H, 6.39; N, 4.23; 0, 14.48; 5, 9.68. Found: C, 65.36; H, 6.40; N, 4.08; S, 9.70.

Preparation of (2R,4R,5S)-3-(2,4,6-mesitylsulfonyl -3,3a,8,8a-tetrahydro-1-oxa-2-thia-3-aza-cyclopentaralindene 2-oxide (32) from (1R,2S)-aminoindanol mesitylene sulfonamide (31): To a 1 L three-necked flask equipped with a mechanical stirrer, an argon inlet, a thermometer probe and rubber septum, was charged (1R,2S)-aminoindanol mesitylene sulfonamide (31 g, 93.7 mmol), THF (50 mL) and the reaction mixture was cooled to –45° C. Thionyl chloride (15.2 g, 128 mmol) was added slowly via syringe in one portion, followed by slow addition of collidine (32 g, 264 mmol) in THF (250 mL) for 6 hours. The reaction was quenched with aqueous NaHCO$_3$ (100 mL), diluted with EtOAc (100 mL) and warmed to room temperature. The organic layer was washed with brine (100 mL), dried with Na$_2$SO$_4$ and concentrated to dryness. The residue was added heptane (150 mL), stirred for 2 hours, and filtered to give a white or off white solid product with 85% de. Crystallization from EtOAc/heptane provided a white solid product. The mother liquor was concentrated, and a second crop of crystals was obtained. This process was repeated two times to give a total yield of 28 g (78%) of (2R,4R,5S)-3-(2,4,6-mesitylsulfonyl)-3,3a,8,8a-tetrahydro-1-oxa-2-thia-3-aza-cyclopenta[a]indene 2-oxide (32) with >99% de.

Preparation of (2S,4S,5R)-3-(2,4,6-mesitylsulfonyl-3,3a,8,8a-tetrahydro-1-oxa-2-thia-3-aza-cyclopenta[a]indene 2-oxide (36) from (1S,2R)-1-amino-2-indanol-N-2,4,6-mesitylsulfonamide (35): The same procedure described above was used to provide the product with 76% yield and >99% de. $^1$H NMR (CDCl$_3$): δ 2.41 (s, 3H), 2.77 (s, 6H), 3.40–3.66 (m, 2H), 5.57 (d, J=6.4 Hz, 1H), 5.86–5.91 (m, 1H), 6.63 (d, J=8.1 Hz, 1H), 7.08–7.34 (m, 5H). $^{13}$C NMR (CDCl$_3$): δ 21.5, 23.4, 39.6, 66.6, 96.0, 125.0, 125.8, 128.1, 129.8, 132.8, 138.8, 141.2, 145.1. Anal. C$_{18}$H$_{19}$NO$_4$S$_2$, Cal: C, 57.27; H, 5.07; N, 3.71; S, 16.99. Found: C, 57.45; H, 5.14; N, 3.76; S, 16.93.

Preparation of aminoindanol 4-toluene sulfonamide (1R,2R,3S)-1,2,3-oxathiazolidine-S-oxide (39) from (1R,2S)-1-amino-2-indanol-N-4-toluenesulfonamide (38) or aminoindanol 4-toluene sulfonamide (1S,2S,3R)-1,2,3-oxathiazolidine-S-oxide (42) from (1S,2R)-1-amino-2-indanol-N-4-toluenesulfonamide (41): The same procedure described above was used to provide the title compound quantitatively with 82% de. Crystallization from heptane/EtOAc furnished the diastereomeric pure product with >99% de (minor diastereomere not detected) and 65% yield. $^1$H NMR (CDCl$_3$): δ 2.51 (s, 3H), 3.32–3.62 (m, 2H), 5.38–5.52 (m, 2H), 7.81–7.89 (m, 6H), 7.81–7.89 (m, 2H). $^{13}$C NMR (CDCl$_3$): δ 22.0, 39.7, 67.1,93.3, 125.6, 126.0, 127.8, 128.1, 130.0, 130.6, 135.9, 138.2, 138.6, 145.6. Anal: C$_{16}$H$_{15}$N$_4$S$_2$, Cal: C, 55.00; H, 4.33; N, 4.01; S, 18.35. Found: C 55.09; H, 4.37; N, 3.92; S, 18.39.

Prepartion of (2S,4R,5S)-3-(4-toluenesulfonyl)-3,3a,8,8a-tetrahydro-1-oxa-2-thia-3-aza-cyclopentaralindene 2-oxide (44) from (1R,2S)-1-amino-2-indanol-N-4-toluenesulfonamide (38): A 250 mL three-necked flask equipped with a mechanical stirrer, an argon inlet, a thermometer probe and rubber septum, was charged (1R,2S)-1-amino-2-indanol-N-4-toluenesulfonamide (10.0 g, 33.0 mmol), THF (30 mL) and the reaction mixture was cooled to –45° C. Thionyl chloride (5.9 g, 49.6 mmol) was added slowly via syringe in one portion, followed by slow addition of 2,6-di-t-butyl pyridine (15.8 g, 80.0 mmol) in THF (100 mL) for 1–2 hours, and the reaction mixture was allowed to warm to room temperature with stirring. After 6–8 hours, as monitored by TLC for disappearance of starting material, the reaction mixture was cooled to –5° C. and quenched with aqueous NaHCO$_3$ (40 mL), diluted with EtOAc (100 mL) and warmed to room temperature. The organic layer was washed with brine (100 mL) and concentrated to dryness. The residue was added heptane (100 mL), stirred for 2 hours, and filtered to give a white or off white solid product (11.0 g, 95.5%) with >97% de (the crude product was used directly in the next step). Crystallization from EtOAc/heptane furnished diastereomeric pure product (>99% de, minor diastereomer not detected).

Preparation of (2R,4S,5R)-3-(4-toluenesulfonyl)-3,3a,8,8a-tetrahydro-1-oxa-2-thia-3-aza-cyclopenta[a]indene 2-oxide (46) from (1S,2R)-1-amino-2-indanol-N-4-toluenesulfonamide (41): The same procedure described above was used to provide the title product with same result. $^1$H NMR (CDCl$_3$): δ 2.46 (s, 3H), 3.31 (s, 2H), 5.02–5.04 (d, J=5.0 Hz, 1H), 5.77–5.82 (m, 1H), 7.22–7.42 (m, 5H), 7.96–8.04 (m, 3H). $^{13}$C NMR(CDCl$_3$): δ 22.0, 36.2, 65.1, 90.6, 125.2, 127.0, 128.9, 129.8, 130.2, 135.5, 137.9, 139.2, 145.5. Anal C$_{16}$H$_{15}$NO$_4$S$_2$ Cal: C, 55.0; H, 4.33; N, 4.01; S, 18.35. Found: C, 55.11; H, 4.35; N, 4.00; S, 18.4.

Preparation of (S)-2-Methyl-2-propylsulfinic acid (1R,2S)-1-(2,4,6-mesitylsulfonylamino)-indan-2-yl ester (33) from (2R,4R,5S)-3-(2,4,6-mesitylsulfonyl)-3,3a,8,8a-tetrahydro-1-oxa-2-thia-3-aza-cyclopentaralindene 2-oxide (32): In a 100 mL two-necked, round-bottomed flask equipped with a magnetic stir bar, rubber septum, and argon inlet was placed (2R,4R,5S)-3-(2,4,6-mesitylsulfonyl)-3,3a,8,8a-tetrahydro-1-oxa-2-thia-3-aza-cyclopenta[a]indene 2-oxide (32) (2.2 g, 5.8 mmol) dissolved in THF (20 mL) and the mixture was cooled to –10° C. A solution of t-butyl magnesium chloride (10.8 mL, 1.0 M) in THF was added dropwise via syringe for 1 hour and the reaction was allowed to warm to room temperature with stirring. After 2 hours, as monitored by TLC for the disappearance of the starting material, the reaction mixture was cooled to 0° C. quenched with aqueous NaHCO$_3$ (10 mL), and diluted with EtOAc (20 mL). The aqueous phase was extracted with EtOAc (10 mL). The combined organic phases were washed with brine (20 mL), dried with Na$_2$SO$_4$ and concentrated to afford a crystalline product (2.45 g, 96.5%) with >99% de (minor diastereomer not detected).

Preparation of (R)-2-Methyl-2-propylsulfinic acid (1S, 2R)-1-(2,4,6-mesitylsulfonylamino)-indan-2-yl ester (37) from (2S,4S,5R)-3-(2,4,6-mesitylsulfonyl)-3,3a,8,8a-tetrahydro-1-oxa-2-thia-3-aza-cyclopenta[a]indene 2-oxide (36): The same procedure described above was used. The result provided 95% yield and >99% de. $^1$H NMR (CDCl$_3$): δ 1.07 (s, 9H), 2.32 (s, 3H), 2.71 (s, 6H), 3.06 (s, 2H), 4.75–4.85 (m, 2H), 5.64 (d, J=9.3 Hz, 1H), 6.99 (s, 1H), 7.17–7.28 (m, 5H). $^{13}$C NMR (CDCl$_3$): δ 21.1, 21.8, 37.8, 58.1, 60.5, 82.7, 124.8, 124.9, 127.8, 128.5, 132.3, 134.6, 137.8, 139.6, 140.3, 142.6. Anal. C$_{22}$H$_{29}$NO$_4$S$_2$: Cal. C, 60.66; H, 6.71; N, 3.22; S, 14.72. Found: C, 60.75; H, 6.72; N, 3.15; S, 14.65.

Preparation of (S)-2-Methyl-2-propylsulfinic acid (1R, 2S)-1-(4-toluenesulfonylamino)-indan-2-yl ester (40) from (2R,4R,5S)-3-(4-toluenesulfonyl)-3,3a,8,8a-tetrahydro-1-oxa-2-thia-3-aza-cyclopenta[a]indene 2-oxide (39) and (R)-tert-butyl (1S,2R) aminoindanol 4-toluene sulfonamide sulfinate (43) from aminoindanol 4-toluene sulfonamide (1S, 2S,3R)-1,2,3-oxathiazolidine-S-oxide (42): The same procedure described above was used to provide the title product with 96% yield and >99% de. $^1$H NMR (CDCl$_3$): δ 1.12 (s, 9H), 2.48 (s, 3H), 2.95–3.14 (m, 2H), 4.64–4.70 (m, 1H), 4.76–4.84 (m, 1H), 5.76 (d, 9.2 Hz, 1H), 7.16–7.50 (m, 6H), 7.94–7.97 (m, 2H). $^{13}$C NMR (CDCl$_3$): δ 21.7, 38.0, 58.2, 60.6, 83.1, 124.9, 124.995, 127.8, 128.6, 130.0, 137.5, 140.1, 143.8. Anal: C$_{20}$H$_{25}$NO$_4$S$_2$. Cal: C, 58.94; H, 6.18; N, 3.44; S, 15.74. Found: C, 59.10; H, 6.22; N, 3.35; S, 15.79.

Preparation of (R)-2-Methyl-2-propylsulfinic acid (1R, 2S)-1-(4-toluenesulfonylamino)-indan-2-yl ester (45) from (2S,4R,5S)-3-(4-toluenesulfonl)-3,3a,8,8a-tetrahydro-1-oxa-2-thia-3-aza-cyclopenta[a]indene 2-oxide (44): In a 100 mL two-necked, round-bottomed flask equipped with a magnetic stir bar, rubber septum, and argon inlet was placed(2S,4R,5S)-3-(4-toluenesulfonyl)-3,3a,8,8a-tetrahydro-1-oxa-2-thia-3-aza-cyclopenta[a]indene 2-oxide (4.5 g, 12.9 mmol) dissolved in THF (30 mL) and the mixture was cooled to 0° C. A solution of t-butyl magnesium chloride (25 mL, 1.0 M) in THF was added dropwise via syringe for 30 minutes with stirring. After 3–4 hours, as monitored by TLC for the disappearance of the starting material, the reaction was quenched with aqueous NaHCO$_3$ (20 mL), and diluted with EtOAc (50 mL). The aqueous phase was extracted with EtOAc (20 mL) and the combined organic phases were washed with brine (40 mL), dried with Na$_2$SO$_4$ and concentrated to afford a crystalline product (5.0 g, 95%) with >99% de (minor diastereomer not detected). $^1$H NMR (CDCl$_3$): δ 1.12 (s, 9H), 2.45 (s, 3H), 3.08–3.26 (m, 2H), 4.84–4.88 (m, 1H), 4.94–4.97 (m, 1H), 5.32 (d, J=10.1 Hz), 7.06–7.35 (m, 6H), 7.83–7.86 (m, 2H). $^{13}$C NMR (CDCl$_3$): δ 21.7, 21.9, 38.6, 58.3, 60.8, 81.8, 124.1, 125.2, 127.3, 127.5, 128.9, 130.0, 138.1, 138.5, 139.2, 143.9.

Preparation of (S)-t-butyl (1R,2S) aminoindanol mesitylene sulfonamide Sulfinate (33) (one pot procedure): A 50 mL three-necked flask equipped with a mechanical stirrer, an argon inlet, a thermometer probe and rubber septum, was charged (1R,2S)-aminoindanol mesitylene sulfonamide (1.22 g, 3.2 mmol), THF (3 mL) and the reaction mixture was cooled to −45° C. Thionyl chloride (0.58 g, 4.9 mmol) was added slowly via syringe in one portion, followed by slow addition of collidine (1.19 g, 9.8 mmol) in THF (10 mL) for 3–4 hours, and the reaction was monitored by TLC. The reaction mixture was warmed to −5° C.–10° C. and stirred for 5 min. The collidine•HCl salt was filtered and the cake washed with THF (4 mL). The filtrate was cooled to −78° C. and tBuMgCl (6.4 mL, 1.0 M) in THF was added slowly. After 4–5 hours, as monitored by TLC for the disappearance of the starting material, aqueous NaHCO$_3$ (10 mL) was added to quench the reaction, diluted with EtOAc (15 mL) and the mixture was allowed to warm to room temperature The organic phase was washed with brine, 10% NaCl and dried (Na$_2$SO$_4$). Removal of the solvent afforded a viscous oil that was added EtOAc (3 mL) and heptane (10 mL) and stirred for 30 minutes. The crystalline precipitate formed was filtered and washed with heptane and dried to afford the title compound (1.2 g, 75%) with >95% de. (The de was measured by $^1$H NMR). $^1$H NMR (CDCl$_3$): δ 1.40 (s, 9H), 2.34 (s, 3H), 2.74 (s, 6H), 3.06–3.08 (s, 2H), 4.77–4.90 (m, 2H), 5.65 (d, J=10 Hz), 7.02 (s, 1H), 7.27–7.37 (m, 5H). $^{13}$C NMR (CDCl$_3$): δ 21.2, 21.8, 37.8, 58.1, 60.5, 82.7, 124.8, 124.9, 127.8, 128.5, 132.3, 134.6, 137.6, 139.6, 140.5, 142.6.

Preparation of (R)-t-butylsulfinamide (8(R): (R)-TBSA) from (S-tert-Butyl (1R,2S)-aminoindanol mesitylene sulfonamide sulfinate (33): A 250 mL three-necked round-bottomed flask equipped with a mechanical stirrer and an ammonia condenser at about −78° C. was charged with 50 mL of liquid ammonia under Ar atmosphere. After the addition of a few crystals of Fe(NO$_3$)$_3$, lithium wire (0.25 g, 35 mmol) was added portion-wise in a controlled manner and the internal temperature was kept around −45° C. When all the lithium was added and a gray suspension was formed, the reaction mixture was cooled to −78° C. and a solution of (S)-t-butyl (1R,2S)-aminoindanol mesitylene sulfonamide sulfinate ester (5 g, 11.5 mmol) in THF (15 mL) was added slowly over a course of 45 min. Once the addition was complete, the mixture was stirred for additional 30–45 min. before NH$_4$Cl (2.8 g) was added. The cold bath was removed, and stirring continued until the mixture reached ambient temperature. The remaining volatile material was removed under reduced pressure. To the remaining residue was added 5 mL water and stirred. EtOAc (50 mL) was added to the mixture and stirred. After separation of the phases, the organic phase was washed with brine (5 mL×2). After removal of the organic solvent, the residue was added water (40 mL) and stirred for 1 hour. The slurry was filtered and the wet cake was washed with water (10 mL). The aqueous filtrate was then saturated with NaCl and extracted with EtOAc (20 mL×3). Removal of the organic solvent afforded (R)-t-butylsulfinamide (0.75 g, 70%) with 97% ee. (HPLC, Chiralpak AS column, 90:10 hexane/ethanol; 1.2 mL/min, 222 inn; (R)-TBSA r$_t$=6.6 min.; (S)-TBSA, r$_t$=9.4 min.). $^1$H NMR (CDCl$_3$): δ 1.18 (s, 9H), 3.82 (br, s, 2H). $^{13}$C NMR(CDCU): δ 22.1, 55.3.

Preparation of (R)-2-Methyl-2-propylsulfinic acid (1S, 2R)-1-(2,4,6-mesitylsulfonylamino)-indan-2-yl ester (37) or from (R)-2-Methyl-2-propylsulfinic acid (1R,2S)-1-(4-toluenesulfonylamino)-indan-2-yl ester (45): The same procedure described above was used to provide the title products with 98% ee and 73% yield or 98% ee and 72% yield, respectively.

5.2. Example 2

Sulfinamide Synthesis Via (1S,2R)-1-(N-Mesitylene Sulfonyl)Amino-1-Phenyl-2-Propanol One method of preparing sulfinamides is represented by Scheme XIII, below:

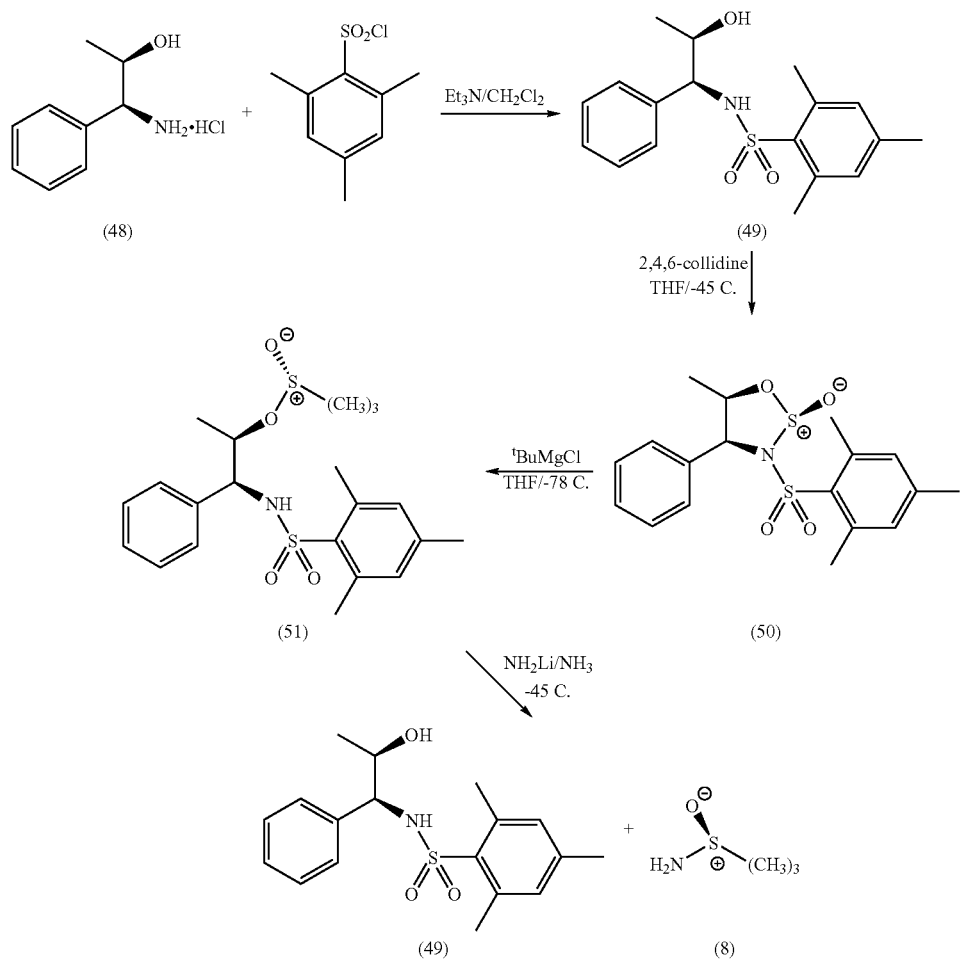

Preparation of (1S,2R)-N-(2-hydroxy-1-phenyl-propyl)-2.4.6-mesitylsulfonamide (49): (1S,2R)-1-amino-1-phenyl-2-propanol (48) (2.0 g, 10.6 mmol) was charged into a 100 mL three neck round-bottomed flask equipped with an overhead stirrer and temperature probe, followed by methylene chloride (20 mL) and the mixture was cooled to 0° C. and stirred for 15 minutes. 2-Mesitylenesulfonyl chloride (2.2 g, 10.1 mmol) was added in one portion and the slurry was mixed for 5 minutes. Triethylamine (2.7 g, 26.7 mmol) was added in 2 hours with stirring and the reaction was monitored by TLC for the disappearance of 2-mesitylenesulfonyl chloride. The reaction was quenched with saturated aqueous NaHCO$_3$ (20 mL) and diluted with EtOAc (20 mL). The organic phase was washed with water (20 mL), 1.0 M HCl (10 mL), water (20 mL) and dried over NaSO$_4$. Evaporation of the organic solvent to dryness provided the title product in 95% yield (3.3 g). $^1$H NMR (CDCl$_3$): δ 1.02 (d, J=6.35 Hz, 3H), 2.14 (d, J=5.49 Hz, 1H), 2.21 (s, 3H), 2.49 (s, 6H), 4.07–4.11 (m, 1H), 4.15–4.18 (m, 1H), 5.70 (d, J=7.21 Hz, 1H), 6.76 (s, 2H), 6.99–7.15 (m, 5H). $^{13}$C NMR (CDCl$_3$): δ 19.5, 21.1, 23.1, 63.0, 70.4, 127.9, 128.3, 132.0, 134.3, 136.7, 139.0, 142.3. Anal: C18H23NO3S. Cal: C, 64.84; H, 6.95; N, 4.20, S, 9.62. Found: C, 65.19; H, 7.04; N, 4.18; S, 9.71.

Preparation of (2S,4S,5R)-5-methyl-4-phenyl-3-(2,4,6-mesitylsulfonyl)-[1,2,3]oxathiazolidine 2-oxide (50): A 50 mL three-necked flask equipped with a mechanical stirrer, an argon inlet, a thermometer probe and rubber septum, was (1S,2R)-N-(2-hydroxy-1-phenyl-propyl)-2,4,6-mesitylsulfonamide (49) (1.89 g, 5.67 mmol), THF (5 mL) and the reaction mixture was cooled to −45° C. Thionyl chloride (1.01 g, 8.50 mmol) was added slowly via syringe in one portion, followed by slow addition of 2,4,6-collidine (2.10 g, 14.18 mmol) in THF (10 mL) for 2–3 hours, and the reaction was monitored by TLC for the disappearance of starting material. The reaction was quenched with saturated aqueous NaHCO$_3$ (10 mL), diluted with EtOAc (20 mL) and the mixture was warmed to room temperature. The organic layer was washed with brine (10 mL) and concentrated to dryness. The residue was added heptane (20 mL), stirred for 2 hours, and filtered to give a white or off white solid product with 94% de. Crystallization from MTBE furnished diastereomeric pure product (1.9 g, 88.5%) with >99% de (minor diastereomer not detected by NMR). $^1$H NMR (CDCl$_3$): δ 1.14 (d, J=6.59 Hz, 3H), 2.16 (s, 3H), 2.52 (s, 6H). 4.87 (d, J=6.72 Hz, 1H), 5.16 (p, J=6.59, 1H), 6.70 (s, 2H), 7.08–7.13 (m, 5H). $^{13}$C NMR (CDCl$_3$): δ 18.07, 21.06, 23.00, 65.34, 87.64, 128.20, 128.28, 131.51, 132.11, 132.93. 140.59, 144.23. Anal: C18H21NO4S2. Cal: C, 56.97; H, 5.58; N, 3.69; S,16.90. Found: C, 57.16; H, 5.62; N, 3.62; S,16.94.

(S)-2-Methyl-2-propylsulfinic acid (1S,2R)-1-methyl-2-phenyl-2-(2,4,6-mesitylsulfonylamino)-ethyl ester (51): In a 50 mL two-necked, round-bottomed flask equipped with a magnetic stir bar, rubber septum, and argon inlet was placed (2S,4S,5R)-5-methyl-4-phenyl-3-(2,4,6-mesitylsulfonyl)-[1,2,3]oxathiazolidine 2-oxide (50) (0.58 g, 1.53 mmol) dissolved in THF (1.0 mL) and the mixture was cooled to −78° C. A solution of t-butyl magnesium chloride (3.1 mL, 1.0 M) in THF was added dropwise via syringe for 30 minutes with stirring. After 1–2 hours, as monitored by TLC for the disappearance of the starting material, the reaction was quenched with saturated aqueous NaHCO$_3$ (5 mL), and diluted with EtOAc (5 mL). The aqueous phase was extracted with EtOAc (4 mL) and the combined organic phases were washed with brine (5 mL), dried with (Na$_2$SO$_4$) and concentrated to afford a crystalline product (0.65 g, 97%) with >99% de (minor diasteriomer not detected). $^1$H NMR (CDCl$_3$): δ 1.080 (d, J=6.47 Hz, 3H), 1.1749 (s, 9H), 2.163 (s, 3H), 2.485 (s, 6H), 4.394 (dd, J1=8.98 Hz, J2=2.32 Hz, 1H), 4.675 (dq, J1=2.32 Hz, J2=6.53 Hz, 1H), 6.61–6.67 (m, 2H), 6.96–7.09 (m, 5H). $^{13}$C NMR (CDCl$_3$): δ 19.10, 20.90, 21.80, 22.98, 57.85, 61.10, 81.86, 127.58, 128.80, 131.61, 134.98, 135.10, 138.50, 141.55.

Preparation of (S)-t-butylsulfinamide ((S)8) from (S)-2-Methyl-2-propylsulfinic acid (1S,2R)-1-methyl-2-phenyl-2-(2,4,6-mesitylsulfonylamino)-ethyl ester (51): A 50 mL three-necked round-bottomed flask equipped with a magnetic stir bar and an ammonia condenser was charged with 30 mL of liquid ammonia under Ar atmosphere. After the addition of a few crystals of Fe(NO$_3$)$_3$, lithium wire (0.05 g, 7.1 mmol) was added in a controlled manner and the internal temperature was kept around −45° C. When all the lithium was added and a gray suspension was formed, the reaction mixture was cooled to −78° C. and a solution of (S)-2-methyl-2-propylsulfinic acid (1S,2R)-1-methyl-2-phenyl-2-(2,4,6-mesitylsulfonylamino)-ethyl ester (51) (0.45 g, 1.03 mmol) in THF (1 mL) was added slowly over a course of 20 minutes. Once the addition was complete, the mixture was warmed to −45° C. and stirred for 1 hour, followed by addition of NH$_4$Cl (0.5 g). The cold bath was removed, and stirring continued until the mixture reached ambient temperature. The remaining volatile material was removed under reduced pressure. To the remaining residue was added 2 mL water and stirred. EtOAc (5 mL) was added to the mixture and stirred. After separation of the phases, the organic phase was washed with brine (2 mL×2). After removal of the organic solvent, the residue was purified by chromatography eluted with EtOAc to afforded (S)-t-butylsulfinamide (0.125 g, 99%) with 99% ee. (HPLC, Chiralpak AS column, 90:10 hexane/ethanol; 1.2 mL/min, 222 nm; (R)-TBSA r$_t$=6.6 min; (S)-TBSA, r$_t$=9.4 min.). $^1$H NMR (CDCl$_3$): δ 1.18 (s, 9H), 3.82 (br, s, 2H). $^{13}$C NMR(CDCl$_3$): δ 22.1, 55.3.

5.3. Example 3

Sulfinamide Synthesis Via (1S,2R)-Norephedrine 4-Toluene Sulfonamide

Another method of preparing sulfinamides is represented by Scheme XIV, below:

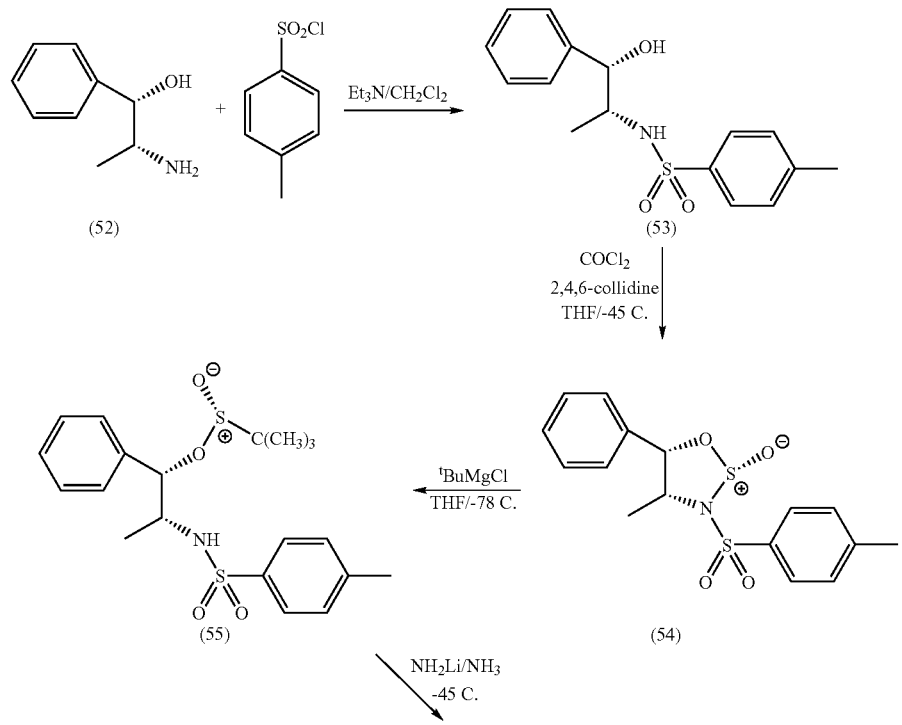

Scheme XIV

-continued

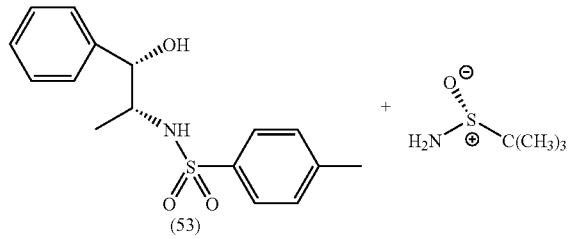

(53)

Preparation of (1S,2R)-N-(1-hydroxy-2-methyl-1phenyl-ethyl)-4-toluene sulfonamide (53): To a 250 mL three neck round-bottomed flask equipped with an overhead stirrer and temperature probe, was charged (1S,2R)-norephedrine (10.0 g, 66.1 mmol), followed by tosyl chloride (12.1 g, 63.6 mmol) and the mixture was cooled to 0° C. and stirred for 15 minutes. Then Et$_3$N was added in 2 hours with stirring and the reaction was monitored by TLC. The reaction was quenched with saturated aqueous NaHCO$_3$ (50 mL). The organic phase was washed with water (50 mL), 1.0 M HCl (25 mL), water (50 mL) and dried over NaSO$_4$. Evaporation of the organic solvent to dryness provided a oily crude product that was crystallized from MTBE/hexane to give the title product (18.5 g) with 90% yield.

(1R,2S)-Norephedrine 4-toluene sulfonamide was prepared by following the same method with 91% yield. $^1$H NMR (CDCl$_3$): δ 0.814 (d, J=6.83 Hz, 3H), 2.40 (s, 3H), 3.116 (d, J=4.76 Hz, 1H), 3.42–3.52 (m, 1H), 4.786–4.812 (m, 1H), 5.138 (d, J=8.67 Hz, 1H), 7.200–7.316 (m, 7H), 7.767 (d, J=8.30 Hz, 2H). $^{13}$C NMR(CDCl$_3$): δ 14.49, 21.66, 55.16, 75.85, 126.19, 127.16, 127.69, 128.41, 129.90, 137.84, 140.48, 143.60.

Preparation of (2R,4R,5S)-4-methyl-5-phenyl-3-(4-toluenesulfonyl-[1,2,3]oxathiazolidine 2-oxide (54): A 100 mL three-necked flask equipped with a magnetic stir bar, an argon inlet, a thermometer probe and rubber septum, was charged (1S,2R)-N-(1-hydroxy-2-methyl-1phenyl-ethyl)-4-toluenesulfonamide (53) (5.2 g, 17.04 mmol), THF (15 mL) and the reaction mixture was cooled to −45° C. Thionyl chloride (3.04 g, 25.5 mmol) was added slowly via syringe in one portion, followed by slow addition of 2,4,6-collidine (6.2 g, 51.2 mmol) in THF (30 mL) for 2–3 hours, and the reaction was monitored by TLC for the disappearance of starting material. The reaction was quenched by addition of NaHCO$_3$ (5.0 g) and saturated aqueous NaHCO$_3$ (20 mL), diluted with EtOAc (40 mL) and the mixture was warmed to room temperature. The organic layer was washed with brine (50 mL), dried over Na$_2$SO$_4$ and concentrated to dryness. The residue was added heptane (50 mL), stirred for 1 hour, and filtered to give a white or off white solid product (5.6 g, 94%) with 97% de. The product was used directly in the next step reaction. Diastereomerically pure compound was obtained by crystallization from MTBE.

(2S,4S,5R)-3-Tosyl-4-methyl-5-phenyl-2-oxo-1,2,3-oxathiazolidine was prepared by following the same method with 93% yield and 97% de. $^1$H NMR (CDCl$_3$): δ 0.868 (d, J=6.97 Hz, 3H), 2.545 (s, 3H), 4.210 (p, J=6.48 Hz, 1H), 5.572 (d, J=5.98 Hz, 1H), 7.284–7.388 (m, 7H), 7.864–7.892 (m, 2H). $^{13}$C NMR (CDCl$_3$): δ 16.59, 21.48, 57.12, 92.14, 126.39, 127.68, 128.86, 129.16, 130.35, 133.41, 136.62, 145.34.

(R)-2-Methyl-2-propylsulfinic acid (1S,2R)-1-phenyl-2-(4-toluenesulfonylamino)propyl ester (55): In a 100 mL two-necked, round-bottomed flask equipped with a magnetic stir bar, rubber septum, and argon inlet was placed (2R,4R,5S)-4-methyl-5-phenyl-3-(4-toluenesulfonyl)-[1,2,3]oxathiazolidine 2-oxide (54) (4.5 g, 12.8 mmol) dissolved in THF (30.0 mL) and the mixture was cooled to −78° C. A solution of t-butyl magnesium chloride (25 mL, 1.0 M) in THF was added dropwise via syringe for 30 minutes with stirring. After 1–2 hours as monitored by TLC for the disappearance of the starting material, the reaction was quenched with aqueous NaHCO$_3$ (30 mL), and diluted with EtOAc (40 mL). The aqueous phase was extracted with EtOAc (20 mL) and the combined organic phases were washed with brine (40 mL), dried with (Na$_2$SO$_4$) and concentrated to afford a crystalline product (5.2 g, 99%) with 97% de.

(S)-2-Methyl-2-propylsulfinic acid (1R,2S)-1-phenyl-2-(4-toluenesulfonylamino)propyl ester was prepared by following the same method with 98% yield and 97% de. $^1$H NMR (CDCl$_3$): δ 0.981 (d, J=6.84 Hz, 3H), 1.251 (s, 9H), 2.428 (s, 3H), 3.56–3.675 (m, 1H), 4.956 (d, J=2.32 Hz, 1H), 5.841 (d, J=9.77 Hz, 1H), 7.073–7.105 (m, 2H), 7.270–7.350 (m, 5H), 7.85–7.879 (m, 2H). $^{13}$C NMR (CDCl$_3$): δ 14.88, 21.67, 21.90, 54.57, 58.34, 84.82, 125.98, 127.31, 128.36, 128.66, 129.86, 137.37, 138.48, 143.46.

Preparation of (R)-t-butylsulfinamide ((R)-TBSA) from (R)-2-Methyl-2-propylsulfinic acid (1S,2R)-1-phenyl-2-(4-toluenesulfonylamino)-propyl ester (55): A 100 mL three-necked round-bottomed flask equipped with a magnetic stir bar and an ammonia ; condenser was charged with 50 mL of liquid ammonia under Ar atmosphere. After the addition of a few crystals of Fe(NO$_3$)$_3$, lithium wire (0.3 g, 42.8 mmol) was added in a controlled manner and the internal temperature was kept around −45° C. When all the lithium was added and a gray suspension was formed, the reaction mixture was cooled to −78° C. and a solution of (S)-t-butyl (1S,2R)-norephedrine sulfinate (2.6 g, 6.3 mmol) in THF (6 mL) was added slowly over a course of 40 minutes. Once the addition was complete, as the reaction was monitored by TLC for the disappearance of the starting material, the mixture was added NH$_4$Cl (4.0 g). The cold bath was removed, and stirring continued until the mixture reached ambient temperature. The remaining volatile material was removed under reduced pressure. To the remaining residue was added 5 mL of water and stirred. EtOAc (50 mL) was added to the mixture and stirred. After separation of the phases, the organic phase was washed with brine (6 mL×2). After removal of the organic solvent, the residue was purified with chromatography eluted with EtOAc to afforded (R)-t-butylsulfinamide (0.65 g, 85%) with 96% ee.

Preparation of (S)-t-butyl sulfinamide from (S)-2-Methyl-2-propylsulfinic acid (1R,2S)-1-phenyl-2-(4-toluenesulfonylamino)-propyl ester: The same procedure described above was followed, an furnished the title product in 86% yield and 96% ee. (HPLC, Chiralpak AS column, 90:10 hexane/ethanol; 1.2 mL/min, 222 nm; (R)-TBSA $r_t$=6.6 min; (S)-TBSA, $r_t$=9.4 min.). $^1$H NMR(CDCl$_3$): δ 1.18 (s, 9H), 3.82 (br, s, 2H). $^{13}$C NMR (CDCl$_3$): δ 22.1, 55.3.

5.4. Example 4

Preparation of Enantiomerically Pure Sulfoxides

Stereomerically pure (e.g., enantiomerically pure) sulfoxides can be readily prepared using methods of the invention. Specific methods are shown below in schemes XV and XVI:

Scheme XV

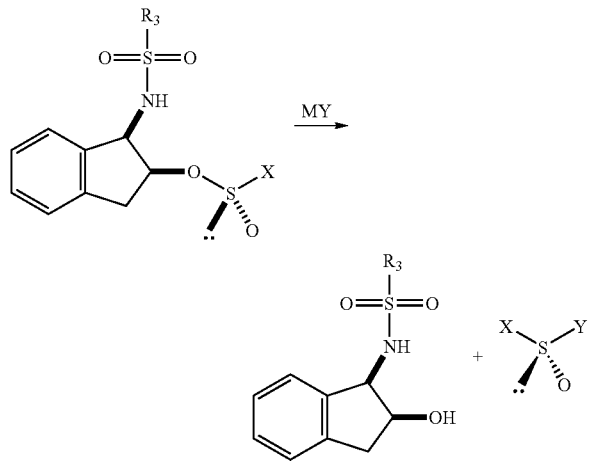

Y = alkyl (linear or branched or cyclic), aryl, hetero atom containing alkyl or aryl group
M = MgHal, or Li; Hal = halogen Scheme XVI

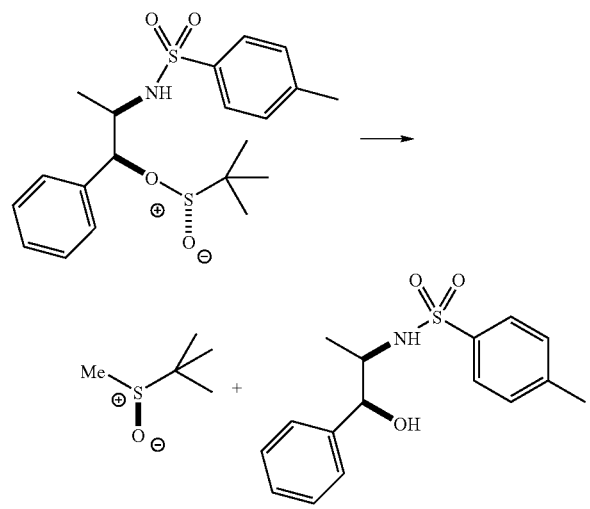

The following can be understood with reference to the schemes shown above.

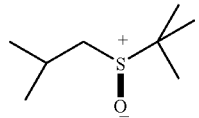

Preparation of (S)-t-butyl isobutyl sulfoxide: A THF (40 mL) solution of (S)-tert-butyl (1R,2S)-aminoindanol mesitylene sulfonamide sulfinate (5.8 g) at −5° C. was slowly added to iBuMgBr (10.5 mL, 2M) in ether. After addition, the reaction mixture was warmed to 10° C., stirred and the reaction was monitored by TLC. The reaction was quenched by aqueous NH$_4$Cl, diluted with EtOAc (20 mL) and stirred. The organic phased was washed with brine (20 mL). Evaporation of the solvent to dryness to afford the crude product that was purified on column eluted with EtOAc to give 1.9 g (88%) title product.

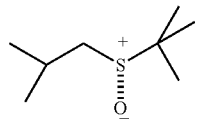

Preparation of (R)-t-butyl isobutal sulfoxide: The same procedure was followed using (R)-tert-butyl (1S,2R)-aminoindanol mesitylene sulfonamide sulfinate, and afforded a 90% yield.

$^1$H NMR (CDCl$_3$): δ 1.24 (s, 9H), 1.086–1.126 (m, 6H), 2.20–2.30 (m, 2H), 2.38–2.45 (m, 1H). $^{13}$C NMR (CDCl$_3$): δ 21.78, 23.06, 23.49, 24.12, 52.63, 55.00, Anal: Cal: C, 59.20; H, 11.18; S, 19.76. Found: C, 59.39; H, 11.36; S, 19.65.

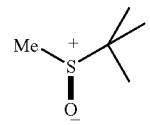

Preparation of (S)-t-butyl methyl sulfoxide from (2S,4S, 5R)-3-(2,4,6-mesitylsulfonyl)-3,3a,8,8a-tetrahydro-1-oxa-2-thia-3-aza-cyclopenta[a]indene 2-oxide (one pot procedure): A solution of (2S,4S,5R)-3-(2,4,6-mesitylsulfonyl)-3,3a,8,8a-tetrahydro-1-oxa-2-thia-3-aza-cyclopenta[a]indene 2-oxide (1.44 g, 3.82 mmol) in THF at −15° C. was slowly added to t-BuMgCl (4.0 mL, 1.0M) in THF, and the reaction mixture was stirred (1–2 hours) until the reaction complete as monitored by TLC. Methyl magnesium bromide (4.4 mL, 1.0 M) in THF was then added, the reaction mixture was warmed to room temperature and stirred for 1–2 hours. The reaction was monitored by TLC. After the reaction mixture was cooled to 0° C., the reaction was quenched by addition of saturated aq. NH$_4$Cl (5 mL), stirred and diluted with EtOAc (5 mL). The aqueous phase was extracted with EtOAc (5 mL×2) and the organic solvent was evaporated. The residue was purified on silica gel eluted with EtOAc/MeOH (8:2) to give the title product (0.38 g, 83%).

Preparation of (S)-t-butyl methyl sulfoxide from (S)-t-Butyl (1S,2R)-norephedrine sulfinate: A THF (2 mL) solution of (S)-t-butyl (1S,2R)-norephedrine sulfinate ester (0.25 g) at −78° C. was added MeMgCl (0.4 mL, 3 M) in THF, and the reaction mixture was warmed slowly to room temperature and stirred. The reaction was monitored by TLC. The reacton was quenched with saturated aqueous NH₄Cl (2 mL), diluted with EtOAc (5 mL) and the organic phase was gently evaporated. The residue was purified on silica gel eluted with EtOAc/MeOH (9:2, v/v) to give 58 mg (79%) title product.

¹H NMR (CDCl₃): δ 1.25 (s, 9H), 2.38 (s, 3). ¹³C NMR (CDCl₃): δ 22.52, 31.60, 52.62.

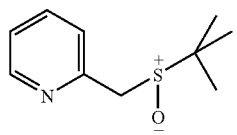

Preparation of (S)-picolinyl t-butylsulfoxide from (S)-tert-Butyl (1R,2S)-aminoindanol 4-toluene sulfonamide sulfinate: To a picolinyl lithium solution (2 mL, 0.6 M) in THF at −78° C. was added (S)-t-butyl-(1R,2S)-aminoindinanol tosylate sulfinate (130 mg, 0.30 mmol). The mixture was warmed to room temperature and stirred until the starting material was consumed as monitored by TLC. The reaction was quenched by aq. NaHCO₃ (20 mL) and diluted with ethyl acetate (20 mL), and the organic phase was washed with water (20 mL) and brine (20 mL). The organic layer was concentrated in vacuo and the residue was purified by chromatography eluted with ethyl acetate to yield 32 mg of the desired product.

¹H NMR (300 MHz, CDCl₃): δ 1.19 (s, 9H), 3.82 (d, 1H, J=12.3 Hz), 4.07 (d, 11H, J=12.3 Hz), 7.26 (m, 1H), 7.45 (d, 1H, J=7.2 Hz), 7.72 (ddd, 1H, J=7.5, 7.5, 1.8 Hz), 8.63 (dd, 1H, J=4.8, 0.9 Hz). ¹³C NMR (75 MHz, CDCl₃): δ 23.29, 54.19, 55.09, 123.19, 132.31, 137.19, 142.77, 150.12.

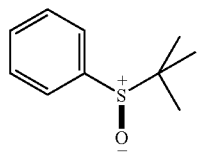

Preparation of (R)-phenyl t-butylsulfoxide from (S)-tert-Butyl (1R,2S)-aminoindanol mesitylene sulfonamide: A 50 mL flask was charged with (S)-tertbutyl-(1R,2S)-aminoindanol mesitylene sulfonamide (1.12 g, 3.0 mmol) and THF (3 mL) and the mixture was cooled to −20° C. To the mixture was added phenylmagnesium bromide (9 mL, 1.0 M in THF), the reaction mixture was stirred at 0° C. and the reaction was monitored by THC. The reaction was quenched by aqueous NaHCO₃ (20 mL) and diluted with ethyl acetate (70 mL), and the organic phase was washed with water (50 mL) and brine (50 mL). The organic layer was concentrated in vacuo and the residue was purified by chromatography eluted by 2:1 hexane:ethyl acetate to give 390 mg of (R)-phenyl t-butylsulfoxide.

¹H NMR (300 MHz, CDCl₃): δ 1.20 (s, 9H), 7.53 (m, 3H), 7.63 (m, 3H). ¹³C NMR (75 MHz, CDCl₃): δ 23.04, 56.02, 126.57, 128.63, 131.40, 140.23. Anal. Calcd for C₁₀H₁₄OS: C, 65.89; H, 7.74; S, 17.59. Found: C, 65.91; H, 7.78; S, 17.65. Optical rotation: C=1.0, CHCl₃ [α]²²_D=+174.6 (lit.=+175).

While the invention has been described with respect to particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method of preparing a sulfinamide or sulfoxide of Formula 2:

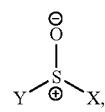

which comprises contacting a compound of Formula 1:

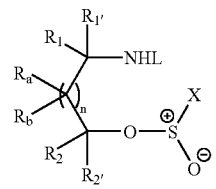

wherein n is 0 to 3; L is $CO_mR_3$ or $SO_mR_3$, wherein m is 0 to 3; $R_1$ and $R_2$ together form a cyclic structure or each of $R_1$ and $R_2$ is independently substituted or unsubstituted alkyl, substituted or unsubstituted aralkyl, substituted or unsubstituted heteroalkyl, substituted or unsubstituted aryl, substituted or unsubstituted heterocycle; $R_1'$ and $R_{2'}$ together form a cyclic structure or each of $R_{1'}$ and $R_{2'}$ is independently hydrogen, substituted or unsubstituted alkyl, substituted or unsubstituted aralkyl, substituted or unsubstituted heteroalkyl, substituted or unsubstituted aryl, or substituted or unsubstituted heterocycle; $R_a$ and $R_b$ together form a cyclic structure or each of $R_a$ and $R_b$ is independently hydrogen, substituted or unsubstituted alkyl, substituted or unsubstituted aralkyl, substituted or unsubstituted heteroalkyl, substituted or unsubstituted aryl, or substituted or unsubstituted heterocycle; and each of $R_3$ and X is independently a polymer bound alkyl, aryl or heteroalkyl, substituted or unsubstituted alkyl, substituted or unsubstituted aralkyl, substituted or unsubstituted heteroalkyl, substituted or unsubstituted aryl, substituted or unsubstituted ether, substituted or unsubstituted ester, substituted or unsubstituted ketone, substituted or unsubstituted phosphonate, substituted or unsubstituted phosphonic acid ester, substituted or unsubstituted phosphinoyl, substituted or unsubstituted sulfide, substituted or unsubstituted sulfone, substituted or unsubstituted sulfinyl imine, substituted or unsubstituted heterocycle, or —NR₄R₅, wherein R₄ and R₅ together with the nitrogen atom to which they are attached form a heterocycle or each of R₄ and R₅ is independently hydrogen, substituted or unsubstituted alkyl, substituted or unsubstituted heteroalkyl, substituted or unsubstituted aralkyl, substituted or unsubstituted aryl, substituted or unsubstituted ether, substituted or unsubstituted sulfide, or substituted or unsubstituted heterocycle;

with a compound of formula MY, wherein M is a metal or metal complex capable of transferring Y to the positively charged sulfur atom of the compound of Formula 1 and Y is independently substituted or unsubstituted alkyl, substituted or unsubstituted aralkyl, substituted or unsubstituted heteroalkyl, substituted or unsubstituted aryl, substituted or unsubstituted ether, substituted or unsubstituted ester, substituted or unsubstituted ketone, substituted or unsubstituted phosphonate, substituted or unsubstituted phosphonic acid ester, substituted or unsubstituted phosphinoyl, substituted or unsubstituted sulfide, substituted or unsubstituted sulfone, substituted or unsubstituted sulfinyl imine, substituted or unsubstituted heterocycle, or is of the formula —$NR_6R_7$, wherein $R_6$ and $R_7$ together with the nitrogen atom to which they are attached form a heterocycle or each of $R_6$ and $R_7$ is independently a polymer bound alkyl, aryl or heteroalkyl; hydrogen; substituted or unsubstituted alkyl; substituted or unsubstituted aralkyl; substituted or unsubstituted heteroalkyl; substituted or unsubstituted aryl; substituted or unsubstituted ether; substituted or unsubstituted ester; substituted or unsubstituted ketone; substituted or unsubstituted phosphonate; substituted or unsubstituted phosphonic acid ester; substituted or unsubstituted phosphinoyl; substituted or unsubstituted sulfide; substituted or unsubstituted sulfone; substituted or unsubstituted sulfinyl imine; substituted or unsubstituted heterocycle; under conditions suitable for the formation of the compound of Formula 2:

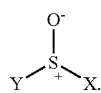

(2)

2. The method of claim 1 wherein the compound of Formula 1 is stereomerically pure.

3. The method of claim 1 wherein the compound of Formula 2 is stereomerically pure.

4. The method of claim 1 wherein M of the formula MY is Al, Ba, Li, Na, K, Ti, Mg, Mn, Zn, Cd, In, Cu, or is of the formula CdZ, BaZ, MgZ, ZnZ, $AlZ_2$, MnZ, InZ, or CuZ, $Ti(OR_1)_3Z$, $Ti(OR_1)_4$, wherein Z is Cl, Br, I, aryl, alkyl, heteroalkyl, aralkyl, or heterocycle and $R_1$ is substituted or unsubstituted alkyl, substituted or unsubstituted aralkyl, substituted or unsubstituted heteroalkyl, substituted or unsubstituted aryl, substituted or unsubstituted heterocycle.

5. The method of claim 1 wherein the compound of Formula 1 is prepared by contacting a compound of Formula 3:

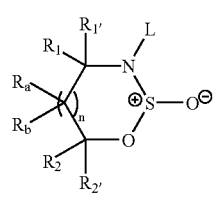

(3)

with a compound of the formula M'X, wherein M' is a metal or metal complex capable of transferring X to the positively charged sulfur atom of the compound of Formula 3.

6. The method of claim 5, wherein M' of the formula M'X is Al, Ba, Li, Na, K, Ti, Mg, Mn, Zn, Cd, In, Cu, or is of the formula CdZ', BaZ', MgZ', ZnZ', $AlZ'_2$, MnZ', InZ', or CuZ', $Ti(OR_1)_3Z'$, $Ti(OR_1)_4$, wherein Z' is Cl, Br, I, aryl, alkyl, heteroalkyl, aralkyl, or heterocycle and $R_1$ is substituted or unsubstituted alkyl, substituted or unsubstituted aralkyl, substituted or unsubstituted heteroalkyl, substituted or unsubstituted aryl, substituted or unsubstituted heterocycle.

7. The method of claim 5, wherein X is tert-butyl, trialkylmethyl, triheteroalkylmethyl, triarylmethyl, triheteroarylmethyl, triheterocyclemethyl, aryl, heterocyclic, heteroaryl, alkyltrialkyl, alkylheteroalkylmethyl, diarylalkylmethyl, adamantyl, dialkyladamantyl, trialkylaryl, triethylmethyl, dimethylethyl, trimethylphenyl, trialkylphenyl, triisopropylphenyl, polymer bound alkyl or aryl or is of Formula 4:

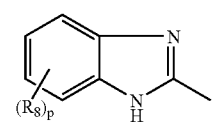

(4)

or a salt thereof, wherein each $R_8$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and p is an integer of 0 to 4; or is of the Formula 5:

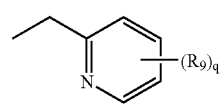

(5)

wherein each $R_9$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and q is an integer of 0 to 4.

8. The method of claim 7 wherein X is of Formula 4 and p is 0 or 1.

9. The method of claim 8 wherein p is 1 and $R_8$ is —$OCH_3$ or —$OCHF_2$.

10. The method of claim 7 wherein X is of Formula 5, q is 2, and each $R_9$ is —$CH_3$, —$OCH_3$, —$OCH_2CF_3$, or —$OC_5H_{11}$.

11. The method of claim 7 wherein X is of Formula 5, q is 3, and $R_9$ is —$CH_3$ or —$OCH_3$.

12. The method of claim 1 wherein Y is —$NR_6R_7$ or is of Formula 4:

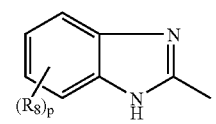

(4)

or a salt thereof, wherein each $R_8$ is independently substituted or unsubstituted alkyl, substituted or unsubstituted heteroalkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and p is an integer of 0 to 4; or is of Formula 5:

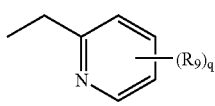

(5)

wherein each $R_9$ is independently substituted or unsubstituted alkyl, substituted or unsubstituted heteroalkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and q is an integer of 0 to 4.

13. The method of claim 12 wherein Y is of Formula 4 and p is 0 or 1.

14. The method of claim 13 wherein p is 1 and $R_8$ is —OCH$_3$ or —OCHF$_2$.

15. The method of claim 12 wherein Y is of Formula 5, q is 2, and each $R_9$ is —CH$_3$, —OCH$_3$, —OCH$_2$CF$_3$, or —OC$_5$H$_{11}$.

16. The method of claim 12 wherein Y is of Formula 5, q is 3, and $R_9$ is —CH$_3$ or —OCH$_3$.

17. The method of claim 1 wherein $R_1$ is aryl or alkyl.

18. The method of claim 1 wherein $R_2$ is aryl or alkyl.

19. The method of claim 1 wherein $R_3$ is a substituted or unsubstituted lower alkyl, substituted or unsubstituted aralkyl, substituted or unsubstituted heteroalkyl, or aryl.

20. The method of claim 19 wherein $R_3$ is 3-mesityl, tolyl, triisopropyl, or a polymer bound alkyl or aryl.

21. The method of claim 1 wherein the compound of Formula 1 has one of the following structures:

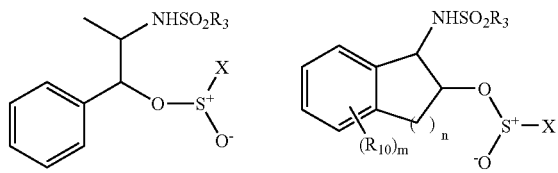

wherein each $R_{10}$ is independently substituted or unsubstituted alkyl, substituted or unsubstituted aralkyl, substituted or unsubstituted aryl, substituted or unsubstituted ether, substituted or unsubstituted sulfide, a primary, secondary, or tertiary amine, a heterocycle, or a halogen atom; n is an integer of 1 to 4; and m is an integer of 0 to 4, and wherein X is tert-butyl, trialkylmethyl, triheteroalkylmethyl, triarylmethyl, triheteroarylmethyl, triheterocyclemethyl, aryl, heterocyclic, heteroaryl, alkyltrialkyl, alkylheteroalkylmethyl, diarylalkylmethyl, adamantyl, dialkyladamantyl, trialkylaryl, triethylmethyl, dimethylethyl, trimethylphenyl, trialkylphenyl, triisopropylphenyl, polymer bound alkyl or aryl or is of Formula 4:

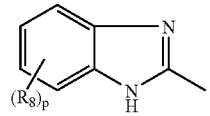

(4)

or a salt thereof, wherein each $R_8$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and p is an integer of 0 to 4; or is of the Formula 5:

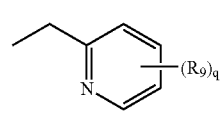

(5)

wherein each $R_9$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and q is an integer of 0 to 4.

22. The method of claim 1 wherein the compound of Formula 2 is of one of the following formulas:

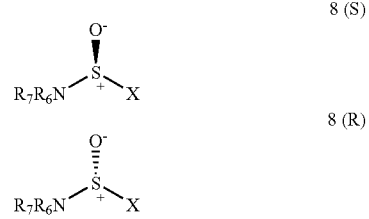

wherein $R_6$ and $R_7$ together with the nitrogen atom to which they are attached form a heterocycle or each of $R_6$ and $R_7$ is independently a polymer bound alkyl, aryl or heteroalkyl; hydrogen; substituted or unsubstituted alkyl; substituted or unsubstituted aralkyl; substituted or unsubstituted heteroalkyl; substituted or unsubstituted aryl; substituted or unsubstituted ether; substituted or unsubstituted ester; substituted or unsubstituted ketone; substituted or unsubstituted phosphonate; substituted or unsubstituted phosphonic acid ester; substituted or unsubstituted phosphinoyl; substituted or unsubstituted sulfide; substituted or unsubstituted sulfone; substituted or unsubstituted sulfinyl imine; substituted or unsubstituted heterocycle.

23. The method of claim 22 wherein X is tert-butyl, trialkylmethyl, triheteroalkylmethyl, triarylmethyl, triheteroarylmethyl, triheterocyclemethyl, aryl, heterocyclic, heteroaryl, alkyltrialkyl, alkylheteroalkylmethyl, diarylalkylmethyl, adamantyl, dialkyladamantyl, trialkylaryl, triethylmethyl, dimethylethyl, trimethylphenyl, trialkylphenyl, triisopropylphenyl, polymer bound alkyl or aryl or is of Formula 4:

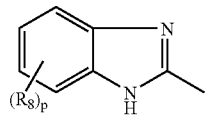

(4)

or a salt thereof, wherein each $R_8$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and p is an integer of 0 to 4; or is of the Formula 5:

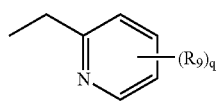

(5)

wherein each $R_9$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, or a halogen atom; and q is an integer of 0 to 4.

24. The method of claim 22 wherein at least one of $R_6$ and $R_7$ is hydrogen.

25. The method of claim 24 wherein $R_6$ and $R_7$ are both hydrogen.

26. The method of claim 5 wherein the compound of Formula 3 has one of the following structures:

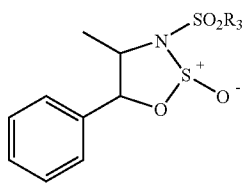

(9)

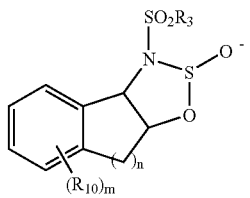

(10)

wherein each $R_{10}$ is independently substituted or unsubstituted alkyl, substituted or unsubstituted aralkyl, substituted or unsubstituted aryl, substituted or unsubstituted ether, substituted or unsubstituted sulfide, substituted or unsubstituted heterocycle, a primary, secondary, or tertiary amine, a heterocycle, or a halogen atom; and m is an integer of 0 to 4, and wherein $R_3$ is aryl, alkyl, or a polymer bound aryl or alkyl.

27. A method as claimed in claim 1, in which the compound of formula (1) is a compound of formula (1A) or (1B)

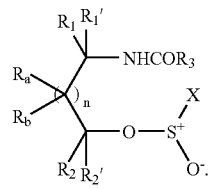

1A

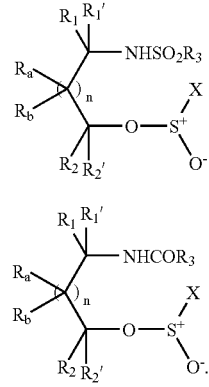

1B

28. A method as claimed in claim 1, in which the compound of formula (1) is stereochemically pure and has one of the following stereochemistries:

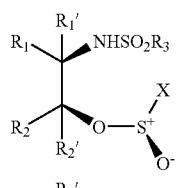 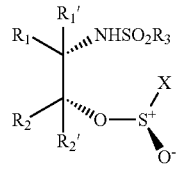

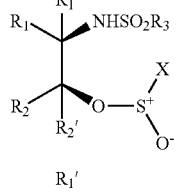 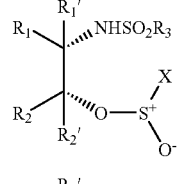

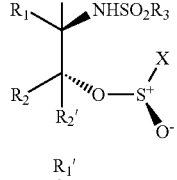 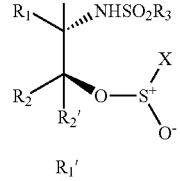

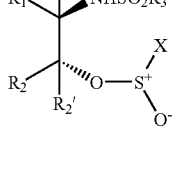 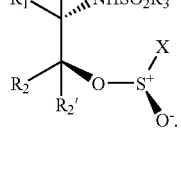

* * * * *

UNITED STATES PATENT AND TRADEMARK OFFICE
CERTIFICATE OF CORRECTION

| | |
|---|---|
| PATENT NO. | : 7,064,214 B2 |
| APPLICATION NO. | : 10/120541 |
| DATED | : June 20, 2006 |
| INVENTOR(S) | : Senanayake et al. |

Page 1 of 1

It is certified that error appears in the above-identified patent and that said Letters Patent is hereby corrected as shown below:

Title page, item (*) Notice: Delete "844 days" and insert --422 days--.

Signed and Sealed this

Thirteenth Day of March, 2007

JON W. DUDAS
*Director of the United States Patent and Trademark Office*